(12) United States Patent
Pepin et al.

(10) Patent No.: US 10,478,617 B2
(45) Date of Patent: Nov. 19, 2019

(54) THIN-FILM ELECTRODE ASSEMBLY WITH SOFT OVERMOLD

(71) Applicant: Verily Life Sciences LLC, Mountain View, CA (US)

(72) Inventors: Brian Pepin, San Francisco, CA (US); Shiv Sabesan, Campbell, CA (US); Bo Lu, Sunnyvale, CA (US)

(73) Assignee: VERILY LIFE SCIENCES LLC, Mountain View, CA (US)

( * ) Notice: Subject to any disclaimer, the term of this patent is extended or adjusted under 35 U.S.C. 154(b) by 1 day.

(21) Appl. No.: 15/597,187

(22) Filed: May 17, 2017

(65) Prior Publication Data

US 2018/0333571 A1 Nov. 22, 2018

(51) Int. Cl.
*A61N 1/00* (2006.01)
*A61N 1/05* (2006.01)
(Continued)

(52) U.S. Cl.
CPC .......... *A61N 1/0551* (2013.01); *A61N 1/056* (2013.01); *A61N 1/0553* (2013.01); *A61N 1/0556* (2013.01); *H01B 3/306* (2013.01); *H01B 3/307* (2013.01); *A61N 1/0526* (2013.01); *A61N 1/3606* (2013.01); *H05K 1/0283* (2013.01); *H05K 2201/09263* (2013.01)

(58) Field of Classification Search
CPC .... A61N 1/0551; A61N 1/056; A61N 1/0553; A61N 1/0556; A61N 1/3606; A61N 1/0526; H01B 3/307; H01B 3/306; H05K 2201/09263; H05K 1/0283
See application file for complete search history.

(56) References Cited

U.S. PATENT DOCUMENTS

| 8,423,143 B2 | 4/2013 | Bartic et al. |
| 2013/0345780 A1 | 12/2013 | Tabada et al. |
| 2015/0157862 A1 | 6/2015 | Greenberg et al. |

FOREIGN PATENT DOCUMENTS

| WO | 2011097160 | 8/2011 |
| WO | 2016090175 | 6/2016 |

OTHER PUBLICATIONS

International Application No. PCT/US2018/024705, "International Search Report and Written Opinion", dated Jun. 15, 2018, 10 pages.
(Continued)

*Primary Examiner* — Scott M. Getzow
(74) *Attorney, Agent, or Firm* — Kilpatrick Townsend & Stockton LLP

(57) ABSTRACT

The present disclosure relates to implantable neuromodulation devices and methods of fabrication, and in particular to a thin-film electrode assemblies and methods of fabricating the thin-film electrode assembly to include a soft overmold. Particularly, aspects of the present invention are directed to a thin-film electrode assembly that includes an overmold and a supporting structure formed within a portion of the overmold. The overmold includes a first polymer and the supporting structure includes a second polymer, different from the first polymer. The thin-film electrode assembly also includes a wire formed within a portion of the supporting structure, and an electrode formed on a top surface of the supporting structure and in electrical contact with the wire. The electrode has a top surface that is raised above a top surface of the overmold by a predetermined distance.

17 Claims, 17 Drawing Sheets

(51) Int. Cl.
*H01B 3/30* (2006.01)
*A61N 1/36* (2006.01)
*H05K 1/02* (2006.01)

(56) References Cited

OTHER PUBLICATIONS

Loeb et al., "Cuff electrodes for chronic stimulation and recording of peripheral nerve activity", Journal of neuroscience methods64.1 (1996): 95-103.

Malachowski et al., "Novel thin film cuff electrode for neural stimulation", Electronics Technology: Integrated Management of Electronic Materials Production, 2003; 26th International Spring Seminar on IEEE, 2003.

Schuettler et al., "Fabrication of implantable microelectrode arrays by laser cutting of silicone rubber and platinum foil", Journal of neural engineering 2.1 (2005): S121.

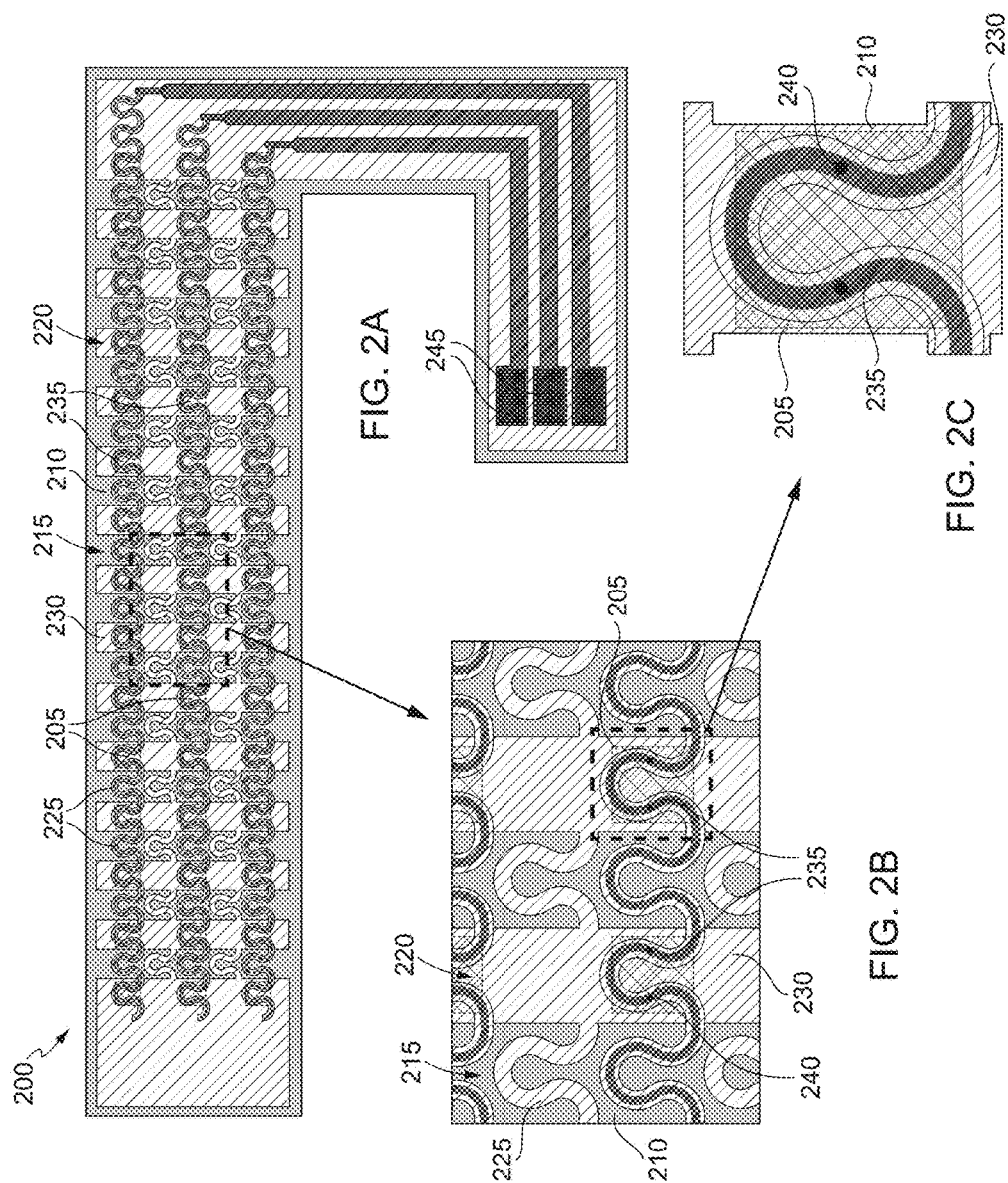

THIN-FILM ELECTRODE ASSEMBLY WITH SOFT OVERMOLD

FIELD OF THE INVENTION

The present disclosure relates to implantable neuromodulation devices and methods of fabrication, and in particular to thin-film electrode assemblies and a methods of fabricating the thin-film electrode assemblies to include a soft overmold.

BACKGROUND

Normal neural activity is an intricate balance of electrical and chemical signals which can be disrupted by a variety of insults (genetic, chemical or physical trauma) to the nervous system, causing cognitive, motor and sensory impairments. Similar to the way a cardiac pacemaker or defibrillator corrects heartbeat abnormalities, neuromodulation therapies help to reestablish normal neural balance. In particular instances, neuromodulation therapies utilize medical device technologies to enhance or suppress activity of the nervous system for the treatment of disease. These technologies include implantable as well as non-implantable neuromodulation devices and systems that deliver electrical, chemical or other agents to reversibly modify brain and nerve cell activity. The most common neuromodulation therapy is spinal cord stimulation to treat chronic neuropathic pain. In addition to chronic pain relief, some examples of neuromodulation therapies include deep brain stimulation for essential tremor, Parkinson's disease, dystonia, epilepsy and psychiatric disorders such as depression, obsessive compulsive disorder and Tourette syndrome; sacral nerve stimulation for pelvic disorders and incontinence; vagus nerve stimulation for rheumatoid arthritis; gastric and colonic stimulation for gastrointestinal disorders such as dysmotility or obesity; vagus nerve stimulation for epilepsy, obesity or depression; carotid artery stimulation for hypertension, and spinal cord stimulation for ischemic disorders such as angina and peripheral vascular disease.

Neuromodulation devices and systems tend to have a similar form factor, derived from their predecessors, e.g. the pacemaker or defibrillator. Such neuromodulation devices and systems typically consist of an implant containing electronics connected to leads that deliver electrical pulses to electrodes interfaced with nerves or nerve bundles via an electrode assembly. The electrode assembly may be formed of a conductive material and typically take the form of book electrodes, cuff electrodes, spiral cuff electrodes, epidural electrodes, helical electrodes, probe electrodes, linear electrodes, paddle electrodes, and intraneural electrodes.

Conventional electrode assemblies may be made out of bulk silicone, which is biocompatible and soft enough to mitigate most tissue damage during normal motion of the assembly against its implanted surroundings. However, as a bulk substrate, silicone is not amenable to conventional techniques for circuit metallization (e.g., screen printing or lithography of metal layers), and as such, current silicone-based electrode assemblies are typically manufactured in cut-and-paste assembly-based processes. The cut-and-paste assembly-based processes dramatically limit the design complexity of the electrode assemblies, for example, the number of electrodes that can be included, the number of layers of metallization, and any three-dimensional features that might be desired. Alternatively, thin-film electrode assemblies made out of polyimide based material exist that use similar metallization technologies to flex-printed circuit board (PCB) fabrication. However, the thin-film electrode assemblies are not suitable for prolonged use as the stiffness of the material, even at thicknesses as low as 75 µm, is in general significantly mismatched with the tissue and may cause scarring, blood clots, and other tissue damage. In view of these factors, the present inventors believe it may be desirable to develop neuromodulation devices and systems that are capable of having design complexity possible with the thin-film electrode assemblies, and the desirable mechanical properties of the silicone-based electrode assemblies.

BRIEF SUMMARY

In one or more embodiments, the invention may relate to a thin-film electrode assembly including an overmold comprising a first polymer, and a supporting structure formed within a portion of the overmold. The supporting structure may comprise a second polymer, different from the first polymer. The thin-film electrode assembly may further include a wire formed within a portion of the supporting structure, and a wire formed within a portion of the supporting structure. The electrode may comprise a top surface that is raised above a top surface of the overmold by a predetermined distance.

In accordance with some aspects of the present disclosure, the first polymer layer may comprise polyimide or liquid crystal polymer (LCP), and the second polymer layer may comprise silicone. Optionally, the top surface of the supporting structure may be coplanar with the top surface of the overmold.

In accordance with some aspects of the present disclosure, the wire may be embedded within the portion of the supporting structure and/or the supporting structure may be embedded within the overmold.

In accordance with other aspects of the present disclosure, the thin-film electrode assembly may further include another supporting structure formed within another portion of the overmold, another wire formed within a portion of the another supporting structure, and another electrode formed on a top surface of the another supporting structure and in electrical contact with the another wire. The another electrode may include a top surface that is raised above the top surface of the overmold by the predetermined distance. The supporting structure and the electrode may be isolated from the another supporting structure and the another electrode by the overmold.

In accordance with other aspects of the present disclosure, the thin-film electrode assembly may further include another supporting structure formed within another portion of the overmold. The supporting structure and the electrode may be isolated from the another supporting structure by the overmold. Optionally, the top surface of the supporting structure may be coplanar with the top surface of the overmold and the top surface of the another supporting structure is coplanar with the top surface of the overmold.

In accordance with some aspects of the present disclosure, the wire may be embedded within the portion of the supporting structure, and the another wire may be embedded within the portion of the another supporting structure. Optionally, the predetermined distance may be greater than 0.5 µm.

In some embodiments, the invention may relates to a thin-film electrode assembly including an overmold comprising silicone, and a first support structure within a first portion of the overmold. The first support structure may includes polyimide or liquid crystal polymer (LCP) and a wire, and the first support structure may have a first shape. The thin-film electrode assembly may further include a second support structure within a second portion of the overmold. The second support structure may include the polyimide or LCP and the wire, and the second support structure may have a second shape that is different from the first shape. The thin-film electrode assembly may further include an electrode formed on a top surface of the first supporting structure and in electrical contact with the wire. The electrode may comprise a top surface that is raised above a top surface of the overmold by a predetermined distance.

In accordance with various aspects of the present disclosure, the thin-film electrode assembly may further include one or more contact pads in electrical contact with the wire, a contact formed within first support structure that provides electrical contact between the electrode and the wire, and/or a third support structure within a third portion of the overmold. Optionally, the third support structure may include the polyimide or LCP, and the third support structure may have the second shape.

In accordance with some aspects of the present disclosure, the first support structure may be in physical contact with the second support structure, and the third support structure may be isolated from the first support structure and the second support structure by the overmold. Optionally, the predetermined distance may be greater than 0.5 μm.

In some embodiments, the invention may relate to a thin-film electrode assembly that includes an overmold including silicone, one or more expandable regions including a first polymer layer and a wiring layer. The first polymer layer may have a first shape that is embedded within the overmold. The thin-film electrode assembly may further include one or more non-expandable regions including a second polymer layer, the wiring layer and at least one electrode. The second polymer layer may have a second shape that is embedded within the overmold, and the second shape may be different from the first shape. The thin-film electrode assembly may further include one or more contact pads in electrical contact with the wiring layer. A top surface of the at least one electrode may be exposed outside of the overmold, the first polymer layer may include polyimide, and the second polymer layer may include polyimide.

In some embodiments, the invention relates to a method of manufacturing a thin-film electrode assembly. The method may include forming a first polymer layer on a first substrate, forming a wiring layer on at least a portion of the first polymer layer, depositing a second polymer layer on the first polymer layer and the wiring layer, forming at least one electrode on at least a portion of the second polymer layer such that the at least one electrode is in contact with at least a portion of a top surface of the wiring layer, detaching an intermediate structure including the first polymer layer, the wiring layer, the second polymer layer, and the at least one electrode from the first substrate, bonding at least a top surface of the at least one electrode to a second substrate, forming a third polymer layer on a bottom surface of the first polymer layer, and detaching the thin-film electrode assembly including the first polymer layer, the wiring layer, the second polymer layer, the at least one electrode, and the third polymer layer from the second substrate.

In accordance with some aspects of the present disclosure, the first polymer layer may include polyimide, the second polymer layer may include polyimide, and the third polymer layer may include silicone. Optionally, the first substrate includes silicon and the second substrate may include silicon.

In some embodiments, the method may further include forming contact vias in the second polymer layer to the wiring layer, and the forming the at least one electrode may include: depositing a conductive material in the contact via and on a top surface of the second polymer layer, and patterning the conductive material to form: (i) a first electrode over a first region of the second polymer layer such that the first electrode is in contact with a first portion of the top surface of the wiring layer, and (ii) a second electrode over a second region of the second polymer layer such that the second electrode is in contact with a second portion of the top surface of the wiring layer.

In accordance with various aspects of the present disclosure, the first region and the second region of the second polymer layer may be separated from one another by a third region of the second polymer layer that does include at least a portion of the wiring layer but does not include an electrode. Optionally, the method may further include forming trenches into the second polymer layer and the first polymer layer to separate the first region and the second region from the third region. The forming the third polymer layer may include depositing and curing of a polymer material directly on the bottom surface of the first polymer layer and the trenches formed in the first polymer layer and the second polymer layer such that a top surface of the third polymer layer in the trenches is coplanar with a top surface of the second polymer layer.

In accordance with some aspects of the present disclosure, the forming of the first polymer layer may include depositing and curing a polymer material directly on the first substrate without an adhesion promoter. Optionally, the bonding the top surface of the at least one electrode to the second substrate may include applying a thermoplastic temporary mounting adhesive to the second substrate to form an adhesive layer on the second substrate, and pressing the top surface of the at least one electrode into the adhesive layer. The detaching the thin-film electrode assembly may include removing the adhesive layer.

In some embodiments, the invention may relates to a method of manufacturing a thin-film electrode assembly. The method may include forming a first polymer layer on a first substrate, forming a wiring layer on at least a portion of the first polymer layer, depositing a second polymer layer on the first polymer layer and the wiring layer, detaching an intermediate structure including the first polymer layer, the wiring layer, and the second polymer layer from the first substrate, bonding a top surface of the intermediate structure to a second substrate, patterning the first polymer layer into regions aligned with the wiring layer, forming a third polymer layer on a bottom surface of the first polymer layer and the second polymer layer, and detaching the thin-film electrode assembly including the first polymer layer, the wiring layer, the second polymer layer, and the third polymer layer from the second substrate.

In accordance with some aspects of the present disclosure, the first polymer layer may include polyimide, the second polymer layer may include silicone, and the third polymer layer may include silicone. Optionally, the first substrate may include silicon and the second substrate may include silicon.

In various embodiments, the forming the wiring layer may include depositing a conductive material on a top surface of the first polymer layer, and patterning the conductive material to form: (i) a first portion of the wiring layer over a first region of the first polymer layer, and (ii) a second portion of the wiring layer over a second region of the first polymer layer. The first region and the second region of the first polymer layer may be separated from one another by a third region of the first polymer layer that does not include the wiring layer.

In accordance with some aspects of the present disclosure, the bonding the top surface of the intermediate structure to the second substrate may include laminating a first side of a temporary mounting adhesive to a top surface of the metal layer and laminating a second side of the temporary mounting adhesive to a top surface of the second substrate. The detaching the thin-film electrode assembly may include removing the temporary mounting adhesive. Optionally, the forming the third polymer layer may include depositing and curing of a polymer material directly on the bottom surface of the first polymer layer and the second polymer layer such that a top surface of the third polymer layer is coplanar with a top surface of the first polymer layer.

BRIEF DESCRIPTION OF THE DRAWINGS

The present invention will be better understood in view of the following non-limiting figures, in which:

FIGS. 2A, 2B, and 2C show an electrode assembly in accordance with some aspects of the present invention;

DETAILED DESCRIPTION

I. Introduction

Figure 1:
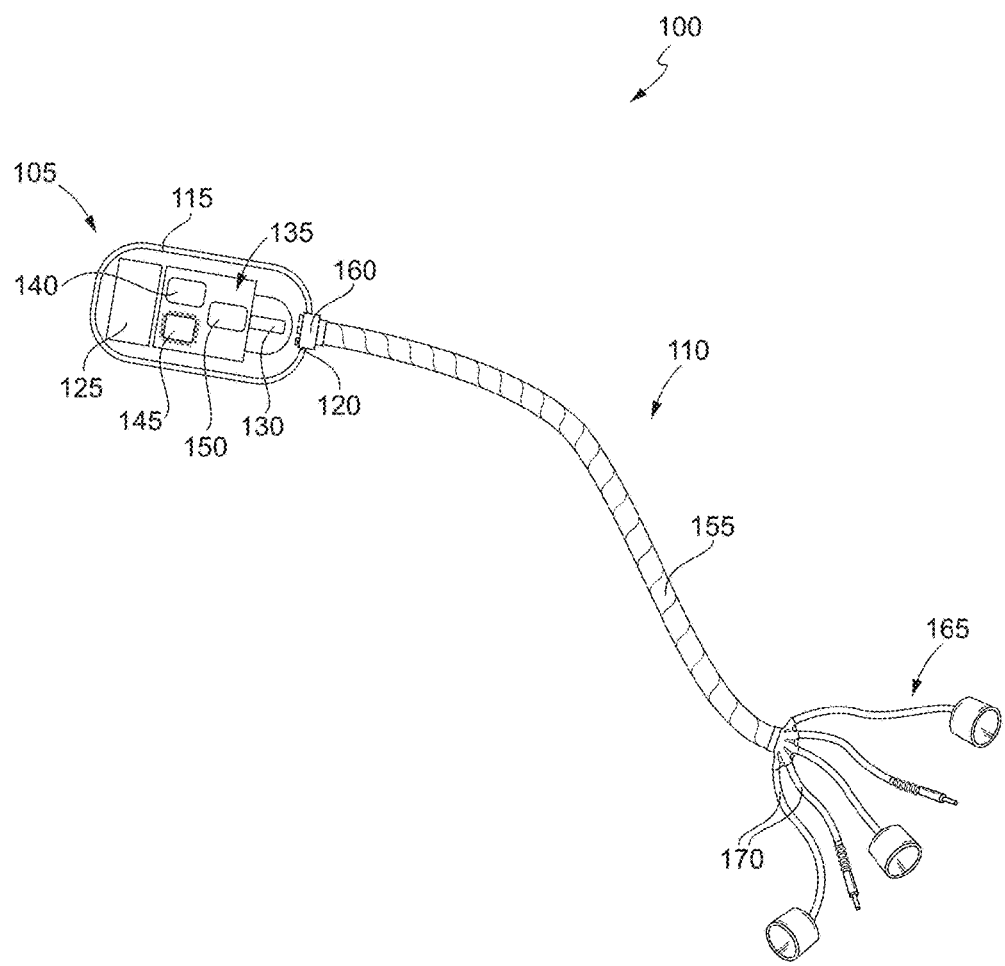
FIG. 1 shows an shows a neuromodulation system in accordance with some aspects of the present invention.

The following disclosure describes thin-film electrode assemblies and methods of fabricating the thin-film electrode assemblies to include a soft overmold. Various embodiments of devices and/or methods of fabrication described herein may be directed toward devices capable of applying or delivering neural stimulation to a patient, thereby possibly 1) influencing, affecting, maintaining, or improving neural stimulation efficacy; and/or 2) influencing, affecting, maintaining, improving, minimizing, or preventing physiological effects caused by the neural stimulation. As used herein, neuromodulation preferably means the alteration of nerve activity through targeted delivery of a stimulus, such as electrical stimulation or chemical agents, to specific neurological sites in the body. A neurostimulator may be a device or system having electronic circuit components and/or software configured to deliver the stimulus to the specific neurological site (e.g., a nerve or artery/nerve plexus) via an electrode assembly. One or more portions of the neurostimulator may be implanted in a patient's body. For example, an implanted pulse generator may be encased in a hermetically sealed housing and surgically implanted in a patient. The electrode assembly may be included as a portion of the housing or provided in a separate location and attached to the pulse generator via one or more leads. The stimulus, stimulation, or neural stimulation may comprise electrical, chemical, optical, ultrasonic, and/or magnetic stimulation signals, and may be defined in accordance with spatial, temporal, electrical, and/or magnetic signal parameters, properties, and/or characteristics. The neural stimulation may generally be delivered or applied to the patient in accordance with a treatment protocol. Typically, the treatment protocol may specify an optimal or best set of parameters directed toward maximally alleviating one or more patient symptoms through neural stimulation applied in a continuous, generally continuous, or nearly continuous manner.

In some embodiments, the present invention may be directed to a thin-film electrode assembly that includes one or more electrodes embedded within a soft overmold such as silicone. Problems associated with conventional thin-film electrode assemblies, however, may include: (i) silicone as a bulk substrate, which may not be amenable to conventional techniques for circuit metallization, and thus dramatically limits the design complexity of the electrode assemblies; (ii) the one or more electrodes are embedded within the silicone in a manner that may leaves a top surface of the one or more electrodes (e.g., the surface intended to make contact with a nerve sheath) below a top surface of the silicone, and thus may result in an inadequate interface with the nerve or artery/nerve plexus; and/or (iii) the polyimide based material as a bulk substrate, which may not be suitable for prolonged use as the stiffness of the material is significantly mismatched with the tissue, and thus may cause scarring, blood clots, and other tissue damage. These conventional thin-film electrode assemblies may be unable to assume greater design complexity while also providing for desirable mechanical properties such as a moisture barrier, biocompatibility, and a soft interface to mitigate most tissue damage during normal motion of the assembly against its implanted surroundings.

In other embodiments, the present invention may be directed to a method of fabricating a thin-film electrode assembly to include one or more electrodes embedded within a soft overmold such as silicone. Problems associated with conventional methods of fabricating the metal/silicone structures, however, may include: (i) depositing and patterning electrodes on a silicone substrate, which may be susceptible to a coefficient of thermal expansion (CTE) mismatch between the material resulting in cracking of the metal; (ii) depositing and patterning electrodes individually and encapsulating the electrodes with silicone, which may require etching to expose a surface of the electrodes and may result in damage to the metal or an undesirable interface between the exposed surface of the electrode and a nerve or artery/nerve plexus; and/or (iii) temporarily mounting a metal film on a silicone substrate, patterning the electrodes, and removing unwanted metal areas by peeling them off of the silicone, which may result in damage to the metal and the temporary mounting does not create a permanent bond between metal and silicone such that moisture permeation is avoided. These systems and approaches can be inefficient and/or ineffective with respect to allowing for greater design complexity while also providing for desirable mechanical properties such as a moisture barrier, biocompatibility, and a soft interface to mitigate most tissue damage during normal motion of the assembly against its implanted surroundings.

In view of these problems, various embodiments disclosed herein are directed to a thin-film electrode assembly that includes one or more thin-film electrodes surrounded by a soft overmold such as silicone. The thin-film may be provided within regions of the soft overmold as a skeleton or a supporting structure for the electronic structures of the assembly such as the electrodes, wiring, and bond/contact pads. The electrodes may be positioned within the soft overmold such that a top surface of the electrodes is raised above or planar with a top surface of the soft overmold. For example, one or more illustrative embodiments of a thin-film electrode assembly may include an overmold and a supporting structure formed within a portion of the overmold. The overmold may include a first polymer and the supporting structure may include a second polymer, different from the first polymer. The thin-film electrode assembly may also include a wire formed within a portion of the supporting structure, and an electrode formed on a top surface of the supporting structure and in electrical contact with the wire. The electrode may have a top surface that is raised above a top surface of the overmold by a predetermined distance. The first polymer layer may comprise polyimide or liquid crystal polymer (LCP), and the second polymer layer may comprise silicone.

To further address these problems, other embodiments may be directed to a method of fabricating a thin-film electrode assembly that may include fabricating thin-film electrodes on a substrate, mounting the thin-film electrodes to a carrier (e.g., electrode side down), depositing a soft overmold such as silicone on a backside of the substrate, and singulation of the new, overmolded device via laser cut, die cut, or similar (e.g., the removal of a single device from the carrier having a plurality of devices). For example, one or more illustrative embodiments of a method of manufacturing a thin-film electrode assembly may include forming a first polymer layer on a first substrate; forming a wiring layer on at least a portion of the first polymer layer; depositing a second polymer layer on the first polymer layer and the wiring layer; forming at least one electrode on at least a portion of the second polymer layer such that the at least one electrode is in contact with at least a portion of a top surface of the wiring layer; detaching an intermediate structure comprising the first polymer layer, the wiring layer, the second polymer layer, and the at least one electrode from the first substrate; bonding at least a top surface of the at least one electrode to a second substrate; forming a third polymer layer on a bottom surface of the first polymer layer; and detaching the thin-film electrode assembly comprising the first polymer layer, the wiring layer, the second polymer layer, the at least one electrode, and the third polymer layer from the second substrate.

Advantageously, these approaches can provide thin-film electrode assemblies and methods of fabricating the thin-film electrode assemblies that are capable of achieving greater design complexity, and a soft interface to mitigate most tissue damage during normal motion of the assembly against its implanted surroundings. Furthermore, the soft interface can be more uniform between the exposed surface of the electrode and a nerve or artery/nerve plexus since the silicone can be deposited while the thin-film electrodes are electrode side down on the carrier and the silicone need not contaminate the front side electrodes (e.g., no need to reopen using an ablation or etching steps). Additionally, the silicone can be plasma treated such that it forms a covalent bond to the polyimide or liquid crystal polymer (LCP) based material to prevent separation of the materials and provide an exceptional moisture barrier.

II. Neuromodulation Devices and Systems with an Electrode Assembly

FIG. 1 shows a neuromodulation system 100 in accordance with some aspects of the present invention. In various embodiments, the neuromodulation system 100 includes an implantable neurostimulator 105 and a lead assembly 110. The implantable neurostimulator 105 may include a housing 115, a feedthrough assembly 120, a power source 125, an antenna 130, and an electronics module 135 (e.g., a computing system). The housing 115 may be comprised of materials that are biocompatible such as bioceramics or bioglasses for radio frequency transparency, or metals such as titanium. In accordance with some aspects of the present invention, the size and shape of the housing 115 may be selected such that the neurostimulator 105 can be implanted within a patient. In the example shown in FIG. 1, the feedthrough assembly 120 is attached to a hole in a surface of the housing 115 such that the housing 115 is hermetically sealed. The feedthrough assembly 120 may include one or more feedthroughs (i.e., electrically conductive elements, pins, wires, tabs, pads, etc.) mounted within and extending through the surface of the housing 115 or a cap from an interior to an exterior of the housing 115. The power source 125 may be within the housing 115 and connected (e.g., electrically connected) to the electronics module 135 to power and operate the components of the electronics module 135. The antenna 130 may be connected (e.g., electrically connected) to the electronics module 135 for wireless communication with external devices via, for example, radiofrequency (RF) telemetry.

In some embodiments, the electronics module 135 may be connected (e.g., electrically connected) to interior ends of the feedthrough assembly 120 such that the electronics module 135 is able to apply a signal or electrical current to leads of the lead assembly 110 connected to exterior ends of the feedthrough assembly 120. The electronics module 135 may include discrete and/or integrated electronic circuit components that implement analog and/or digital circuits capable of producing the functions attributed to the neuromodulation devices or systems such as applying or delivering neural stimulation to a patient. In various embodiments, the electronics module 135 may include software and/or electronic circuit components such as a pulse generator 140 that generates a signal to deliver a voltage, current, optical, or ultrasonic stimulation to a nerve or artery/nerve plexus via electrodes, a controller 145 that determines or senses electrical activity and physiological responses via the electrodes and sensors, controls stimulation parameters of the pulse generator 140 (e.g., control stimulation parameters based on feedback from the physiological responses), and/or causes delivery of the stimulation via the pulse generator 140 and electrodes, and a memory 150 with program instructions operable on by the pulse generator 140 and the controller 145 to perform one or more processes for applying or delivering neural stimulation.

The lead assembly 110 may include a lead body 155, a lead connector 160, an electrode assembly 165, and optionally one or more sensors. In some embodiments, the lead connector 160 may be bonding material that bonds conductor material of the lead body 155 to the electronics module 135 of the implantable neurostimulator 105 via the feedthrough assembly 120. The bonding material may be a conductive epoxy or a metallic solder or weld such as platinum. In other embodiments, the lead connector 160 may be conductive wire or tab (e.g., a wire or tab formed of copper, silver, or gold) that bonds conductor material of the lead body 155 to the electronics module 135 of the implantable neurostimulator 105. In alternative embodiments, the implantable neurostimulator 105 and the lead body 155 may be designed to connect with one another via a lead connector 160 such as a pin and sleeve connector, snap and lock connector, flexible printed circuit connectors, or other means known to those of ordinary skill in the art.

The lead body 155 may include one or more leads 170 of conductive material and insulator. The one or more leads 170 may carry electrical conductors that allow electrical coupling of the electronics module 135 to electrodes of the electrode assembly 165 via the lead connector 160. In some examples the one or more leads 170 may be extruded with a dielectric material such as a polymer having suitable dielectric, flexibility and biocompatibility characteristics. Polyurethane, polycarbonate, silicone, polyethylene, fluoropolymer and/or other medical polymers, copolymers and combinations or blends can be used. In some embodiments, the conductive material for the one or more leads may serve as a strengthening member onto which the body of the lead is extruded. For example, a distal electrode assembly may couple to a centrally located wire on which the body of lead is extruded. The conductive material may be any suitable conductor such as stainless steel, silver, copper or other conductive materials, which may have separate coatings or sheathing for anticorrosive, insulative and/or protective reasons. The conductive material may take various forms including wires, drawn filled tubes, helical coiled conductors, microwires, and/or printed circuits, for example.

FIGS. 2A-2C show an electrode assembly 200 in accordance with some aspects of the present invention. In various embodiments, the electrode assembly 200 may include one or more electrodes 205 and an overmold 210 fabricated in accordance with aspects of the present invention. The electrode assembly 200 may be connected to conductor material of a lead body (e.g., a lead body 155 as described with respect to FIG. 1) via a lead (e.g., one or more leads 170 as described with respect to FIG. 1). In some embodiments, a distal end of the lead carries an electrode assembly 200 (e.g., book electrodes, split cuff electrodes, spiral cuff electrodes, epidural electrodes, helical electrodes, probe electrodes, linear electrodes, neural probe, paddle electrodes, and intraneural electrodes). In other embodiments, a distal end of the lead may carry a plurality of electrode assemblies 200. The overmold 210 may be comprised of a medical grade polymer material, for example, a soft polymer such as silicone or a polymer dispersion such as latex.

The electrode assembly 200 may include one or more expandable portions 215 and one or more non-expandable portions 220. The one or more expandable portions 215 may include a polymer material 225 formed in the shape of a structure (e.g., a serpentine) that allows for the electrode assembly 200 to be expanded, contracted, opened, or closed in order to position the electrode assembly 200 on a nerve or artery/nerve plexus and to allow for the electrode assembly 200 to move with tissue of a patient's body. In various embodiments, the polymer material 225 may be a polymer of imide monomers (i.e., a polyimide) or a liquid crystal polymer (LCP) such as Kevlar®.

The one or more non-expandable portions 220 may include a polymer material 230 formed in the shape of a structure (e.g., an island) that may provide support for microelectronic structures including the one or more electrodes 205, wiring layer 235, optional contacts 240, and bond/contact pads 245. In various embodiments, the polymer material 230 may be the same material as the polymer material 225, for example, a polymer of imide monomers (i.e., a polyimide) or an LCP. In other embodiments, the polymer material 230 may be a different material from that of the polymer material 225, for example, other thermoset plastics such as epoxies, polyesters, silicones, and phenolics.

The wiring layer 235 may be embedded within or located on a surface of the polymer material 225 and/or the polymer material 230 (e.g., FIGS. 2A, 2B, and 2C illustrate the wiring layers 235 as being embedded within the polymer material 225 and/or the polymer material 230, and for an easier understanding of the figures the one or more electrodes 205, the polymer material 225, and/or the polymer material 230 are illustrated in FIGS. 2A, 2B, and 2C with some degree of transparency in order to show the underlying wiring layer 235). The wiring layer 235 may be used to electrically connect the one or more electrodes 205 with the bond/contact pads 245, and ultimately connect the one or more electrodes 205 to the conductor material of a lead body (e.g., a lead body 155 as described with respect to FIG. 1) via a lead in contact with the bond/contact pads 245. In some embodiments, the one or more electrodes 205 may make electrical contact with the wiring layer 235 by using the contacts 240.

In various embodiments, the thin-film electrode assembly 200 may comprise the overmold 210, and one or more expandable portions or regions 215 comprising the first polymer layer 225 and the wiring layer 235. As shown, the first polymer layer 225 has a first shape (e.g., a serpentine shape) that is embedded within the overmold housing 210. The thin-film electrode assembly 200 may further comprise one or more non-expandable portions or regions 220 comprising a second polymer layer 230, the wiring layer 235, and at least one electrode 205. As shown, the second polymer layer 230 has a second shape (e.g., an island or block) that is embedded within the overmold 210, and the second shape is different from the first shape. The thin-film electrode assembly 200 may further comprise one or more contact pads 245 in electrical contact with the wiring layer 235. A top surface of the at least one electrode 205 may be exposed outside of the overmold housing 210, the first polymer layer 225 may comprise polyimide or an LCP, and the second polymer layer 230 may comprise polyimide or an LCP.

As shown in FIGS. 2A-2C, the one or more expandable portions 215 and one or more non-expandable portions 220 may be formed in one or more regions 250 of the electrode assembly 200 as a repeating pattern comprising a region 255 of one or more expandable portions 215 followed by a region 260 of one or more non-expandable portions 220 followed by another region 265 of one or more expandable portions 215. This repeating pattern may be used to form an interface for the electrode assembly 200 that is capable of expanding, contracting, opening, or closing in order to position the electrode assembly 200 on a nerve or artery/nerve plexus and to allow for the electrode assembly 200 to move with tissue of a patient's body, while also providing enough support such that complex microelectronic structures can be incorporated into the electrode assembly 200.

Figure 3A:
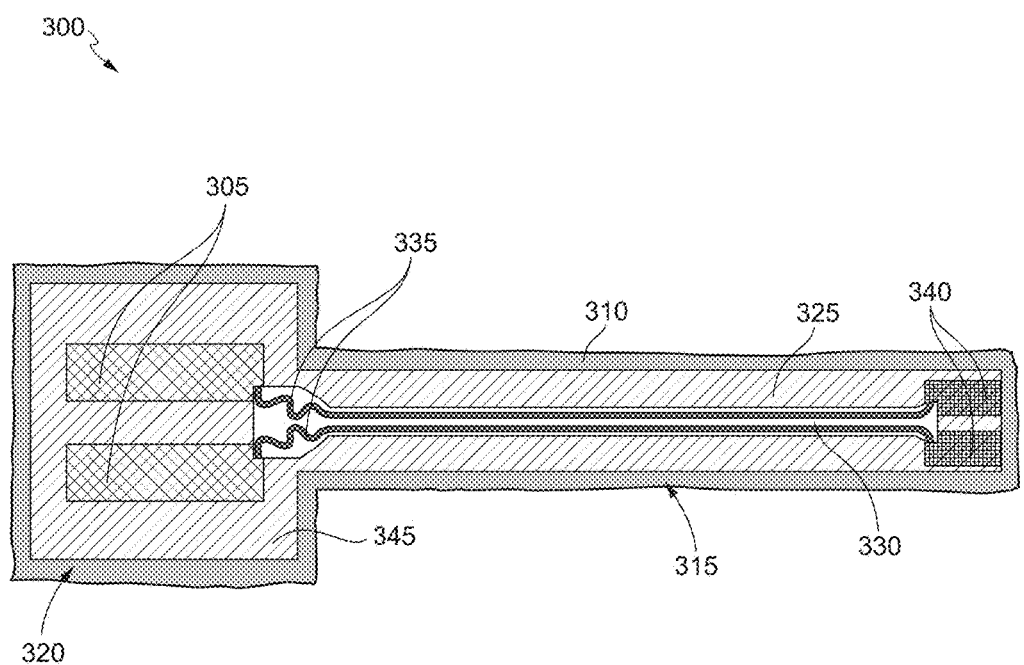
FIGS. 3A, 3B, and 3C show an alternative electrode assembly in accordance with some aspects of the present invention.
Figure 3B:
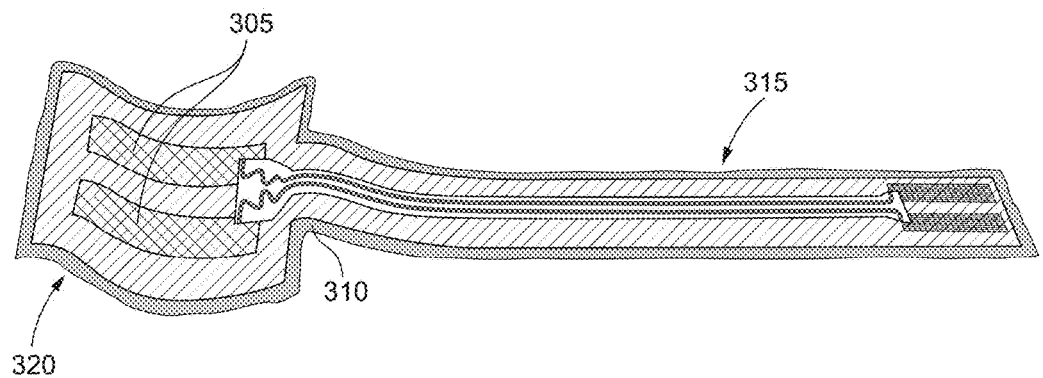
Figure 3C:
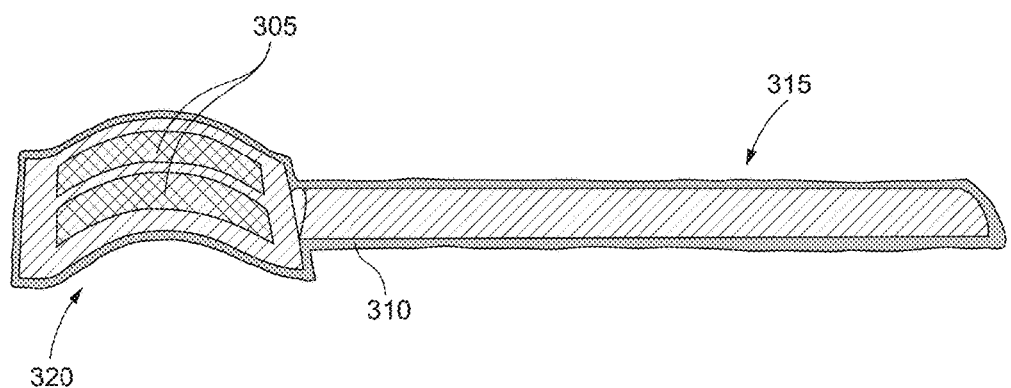

FIGS. 3A-3C show an alternative electrode assembly 300 in accordance with some aspects of the present invention. In various embodiments, the electrode assembly 300 may include one or more electrodes 305 and an overmold 310 fabricated in accordance with aspects of the present invention. The electrode assembly 300 may be connected to conductor material of a lead body (e.g., a lead body 155 as described with respect to FIG. 1) via a lead (e.g., one or more leads 170 as described with respect to FIG. 1). In some embodiments, a distal end of the lead may carry an electrode assembly 300 (e.g., book electrodes, split cuff electrodes, spiral cuff electrodes, epidural electrodes, helical electrodes, probe electrodes, linear electrodes, neural probe, paddle electrodes, and intraneural electrodes). In other embodiments, a distal end of the lead may carry a plurality of electrode assemblies 300. The overmold 310 may be comprised of a medical grade polymer material, for example, a soft polymer such as silicone or a polymer dispersion such as latex.

The electrode assembly 300 may include a planar portion 315 and a curled portion 320. The planar portion 315 may include a polymer material 325 formed in the shape of a structure (e.g., a straight line) that provides support for microelectronic structures including wiring layer 330, optional contacts 335, and bond/contact pads 340. In various embodiments, the polymer material 325 may be a polymer of imide monomers (i.e., a polyimide) or a liquid crystal polymer (LCP) such as Kevlar®. The curled portion 320 may include a polymer material 345 formed in the shape of a structure (e.g., an arc or curl) that allows for the electrode assembly 300 to be opened or closed in order to position the electrode assembly 300 on a nerve or artery/nerve plexus and to allow for the electrode assembly 300 to move with tissue of a patient's body. The polymer material 345 may also provides support for microelectronic structures including the one or more electrodes 305 and optional contacts 335. In various embodiments, the polymer material 345 may be the same material as the polymer material 325, for example, a polymer of imide monomers (i.e., a polyimide) or an LCP. In other embodiments, the polymer material 345 may be a different material from that of the polymer material 325, for example, other thermoset plastics such as epoxies, polyesters, silicones, and phenolics.

The wiring layer 330 may be embedded within or located on a surface of the polymer material 325 and/or the polymer material 345 (e.g., FIGS. 3A, 3B, and 3C illustrate the wiring layers 330 as being embedded within the polymer material 325, and for an easier understanding of the figures the one or more electrodes 305, the polymer material 325, and/or the polymer material 335 are illustrated in FIGS. 3A, 3B, and 3C with some degree of transparency in order to show the underlying wiring layer 330). The wiring layer 330 may be used to electrically connect the one or more electrodes 305 with the bond/contact pads 340, and ultimately connect the one or more electrodes 305 to the conductor material of a lead body (e.g., a lead body 155 as described with respect to FIG. 1) via a lead in contact with the bond/contact pads 340. In some embodiments, the one or more electrodes 305 may make electrical contact with the wiring layer 330 by using the contacts 335.

Figure 4A:
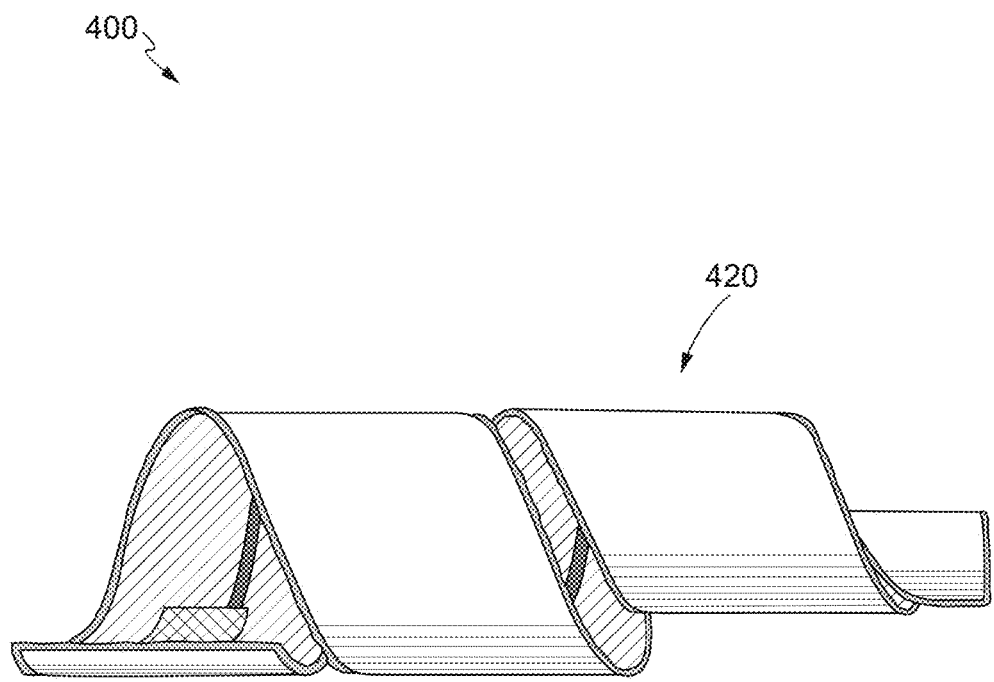
FIGS. 4A, 4B, and 4C show an alternative electrode assembly in accordance with some aspects of the present invention.
Figure 4B:
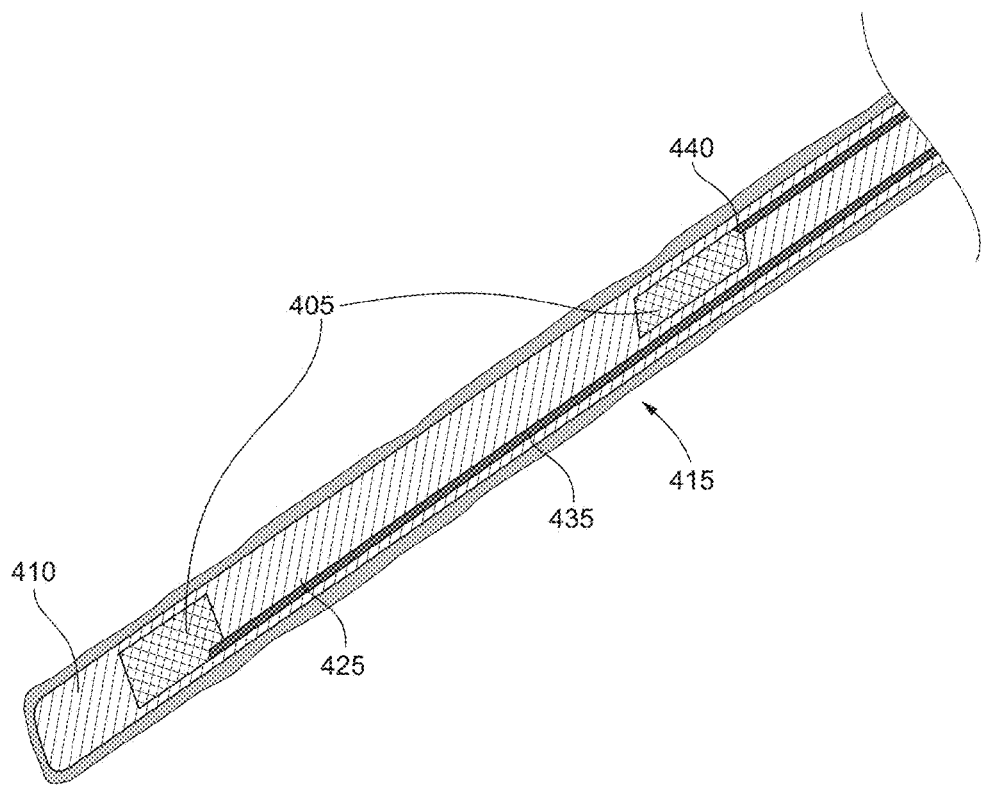
Figure 4C:
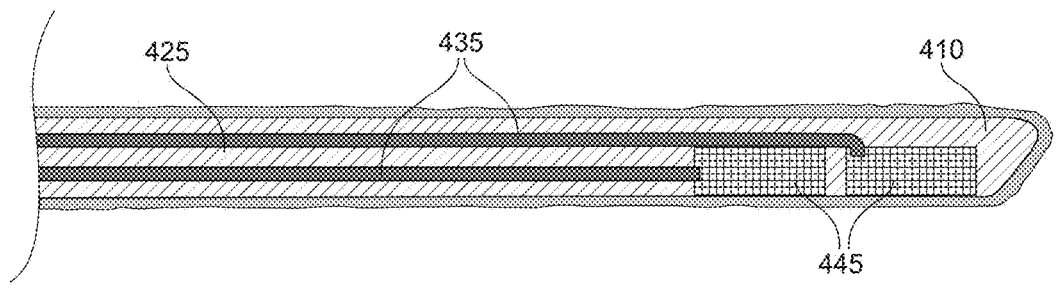

FIGS. 4A-4C show an alternative electrode assembly 400 in accordance with some aspects of the present invention. In various embodiments, the electrode assembly 400 may include one or more electrodes 405 and an overmold 410 fabricated in accordance with aspects of the present invention. The electrode assembly 400 may be connected to conductor material of a lead body (e.g., a lead body 155 as described with respect to FIG. 1) via a lead (e.g., one or more leads 170 as described with respect to FIG. 1). In some embodiments, a distal end of the lead may carry an electrode assembly 400 (e.g., book electrodes, split cuff electrodes, spiral cuff electrodes, epidural electrodes, helical electrodes, probe electrodes, linear electrodes, neural probe, paddle electrodes, and intraneural electrodes). In other embodiments, a distal end of the lead may carry a plurality of electrode assemblies 400. The overmold 410 may be comprised of a medical grade polymer material, for example, a soft polymer such as silicone or a polymer dispersion such as latex.

The electrode assembly 400 may include a planar portion 415 that is thermoformed into a helical shape 420. The planar portion 415 may include a polymer material 425 formed in the shape of a structure (e.g., a straight line) that provides support for microelectronic structures including the one or more electrodes 405, wiring layer 435, optional contacts 440, and bond/contact pads 445. In various embodiments, the polymer material 425 may be a polymer of imide monomers (i.e., a polyimide) or a liquid crystal polymer (LCP) such as Kevlar®.

The wiring layer 435 may be embedded within or located on a surface of the polymer material 425 (e.g., FIGS. 4A, 4B, and 4C illustrate the wiring layer 435 as being embedded within the polymer material 425, and for an easier understanding of the figures the one or more electrodes 405 and the polymer material 425 are illustrated in FIGS. 4A, 4B, and 4C with some degree of transparency in order to show the underlying wiring layer 435). The wiring layer 435 may be used to electrically connect the one or more electrodes 405 with the bond/contact pads 440, and ultimately may connect the one or more electrodes 405 to the conductor material of a lead body (e.g., a lead body 155 as described with respect to FIG. 1) via a lead in contact with the bond/contact pads 440. In some embodiments, the one or more electrodes 405 may make electrical contact with the wiring layer 435 by using the contacts 440.

While the electrode assemblies 200, 300, and 400 have been described at some length and with some particularity with respect to a specific design and/or performance need, it is not intended that the electrode assemblies 200, 300, and 400 be limited to any such particular design and/or performance need. Instead, it should be understood the electrode assemblies 200, 300, and 400 are exemplary embodiments, and that the electrode assemblies 200, 300, and 400 are to be construed with the broadest sense to include variations of the specific design and/or performance need described herein, as well as other variations that are well known to those of skill in the art. In particular, the shape and location of components and layers in the electrode assemblies 200, 300, and 400 may be adjusted or modified to meet specific design and/or performance needs. Furthermore, it is to be understood that other structures may have been omitted from the description of the electrode assemblies 200, 300, and 400 for clarity. The omitted structures may include, for example, sensor structures, insulating layers, interconnect components, passive devices, etc.

Figure 5:
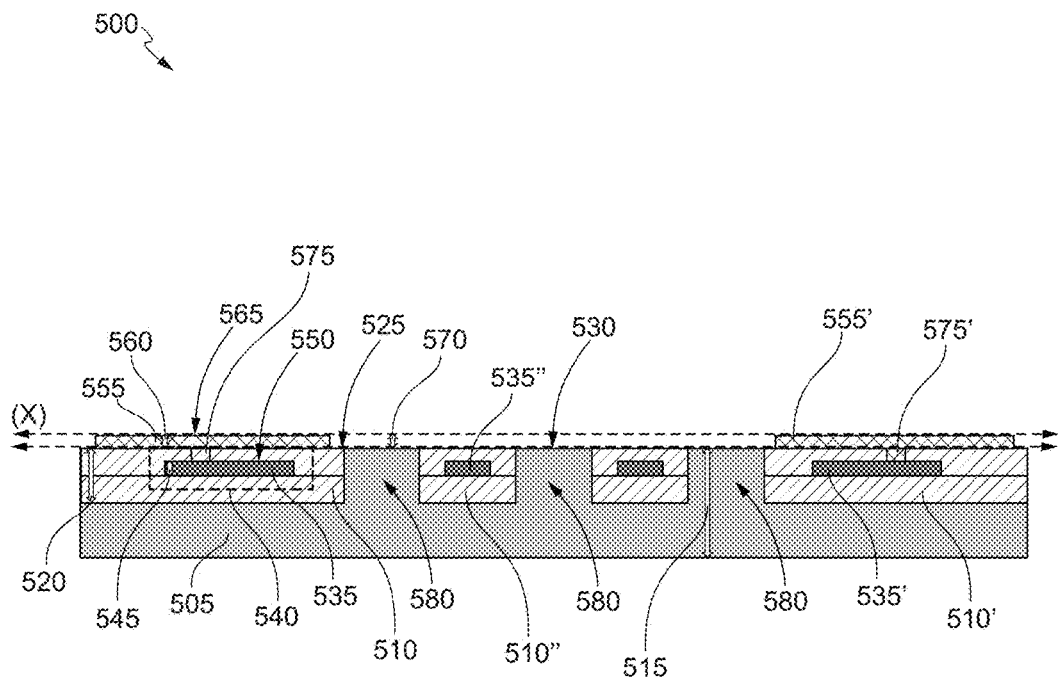
FIG. 5 shows a cross-sectional side view of a portion of an electrode assembly in accordance with some aspects of the present invention.

FIG. 5 shows a cross section of an electrode assembly 500 (e.g., as described with respect to FIG. 2, 3, or 4) fabricated in accordance with aspects of the present invention. In various embodiments, the electrode assembly 500 may include an overmold 505 and a supporting structure 510 formed within a portion of the overmold 505. The overmold 505 may be comprised of a medical grade polymer material, for example, a soft polymer such as silicone or a polymer dispersion such as latex. The supporting structure 510 may be comprised of a polymer of imide monomers (i.e., a polyimide) or a liquid crystal polymer (LCP) such as Kevlar®. The overmold 505 may have a thickness 515 of from 100 µm to 2000 µm, from 150 µm to 1000 µm, from 200 µm to 700 µm, or from 300 µm to 550 µm. The supporting structure 510 may have a thickness 520 of from 0.5 µm to 50 µm, from 1 µm to 40 µm, from 5 µm to 35 µm, or from 10 µm to 25 µm.

In some embodiments, a top surface 525 of the supporting structure 510 may be coplanar ("x") with a top surface 530 of the overmold 505. The term "top surface", as used herein, may defined as being the surface of the material that is facing the targeted substrate for delivery of a stimulus (e.g. nerve or artery/nerve plexus). The term "coplanar", as used herein, may defined as being substantially within the same plane (i.e., a flat surface which extends without end in all directions). In other embodiments, the supporting structure 510 may be embedded within the overmold 505. The term "embedded", as used herein, may be defined as being substantially surrounded on all sides. Substantially, as used herein, may be understood to mean as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes any of 0.1, 1, 5, and 10 percent.

The electrode assembly 500 may further include a wire 535 formed within or on a portion 540 of the supporting structure 510. The wire 535 may be comprised of various metals or alloys thereof, for example, copper (Cu), gold (Au), silver (Ag), gold/chromium (Au/Cr), etc. The wire 535 may have a thickness 545 of from 0.1 µm to 20 µm, from 0.3 µm to 15 µm, from 0.5 µm to 10 µm, or from 0.5 µm to 5 µm. In some embodiments, a top surface 550 of the wire 535 may be coplanar with a top surface 525 of the supporting structure 510. In other embodiments, the wire 535 may be embedded within the supporting structure 510. In yet other embodiments, the wire 535 may be formed on the top surface 525 of the supporting structure 510 and the top surface 550 of the wire 535 may be raised above the top surface 525 of the supporting structure 510.

The electrode assembly 500 may further include an electrode 555 formed on the supporting structure 510 and in electrical contact with the wire 535. The electrode 555 may be comprised of conductive material such as copper (Cu), gold (Au), silver (Ag), titanium (Ti), or platinum (Pt), or alloys thereof such as gold/chromium (Au/Cr) or Titanium/Platinum (Ti/Pt), for example. The electrode 555 may have a thickness 560 of from 0.1 µm to 50 µm, from 0.3 µm to 30 µm, from 0.5 µm to 20 µm, or from 1 µm to 15 µm. In some embodiments, the electrode 555 may comprise a top surface 265 that is raised above the top surface 530 of the overmold 505 by a predetermined distance 570. The predetermined distance 570 may be greater than 0.1 µm, greater than 0.5 µm, greater than 1 µm or greater than 10 µm, or the predetermined distance 570 may be from 0.1 µm to 50 µm, from 0.3 µm to 40 µm, from 0.5 µm to 30 µm, or from 1 µm to 25 µm. In other embodiments, the electrode 555 may comprise a top surface 565 that is coplanar with the top surface 530 of the overmold 505. The electrode 555 may be formed directly on the supporting structure 510. The term "directly", as used herein, may be defined as being without something in between. Alternatively, the electrode 555 may be formed indirectly on the supporting structure 510. The term "indirectly", as used herein, may be defined as having something in between.

The electrode assembly 500 may further include a contact 575 formed within or on the supporting structure 510 that provides the electrical contact between the electrode 555 and the wire 535. The contact 575 may be comprised of conductive material such as copper (Cu), gold (Au), silver (Ag), titanium (Ti), or platinum (Pt), or alloys thereof such as gold/chromium (Au/Cr) or Titanium/Platinum (Ti/Pt), for example.

In various embodiments, the electrode assembly 500 may comprise one or more additional supporting structures that may support one or more additional electronic structures of the assembly such as an electrode, wire, and bond/contact pad. The supporting structures and electronic structures may be isolated from one another by region(s) 580 of the overmold 505. For example, as shown in FIG. 5, the electrode assembly 500 may further comprise one or more of supporting structure 510', supporting structure 510", wire, 535', wire, 535", electrode 555', and contact 575'. The properties of the supporting structures and electronic structures (e.g., thickness, material, position, contact, etc.) may be the same or different from those of the structures previously discussed herein with reference to FIG. 5. However, it should be understood the electrode assembly 500 is an exemplary embodiment, and that the electrode assembly 500 is to be construed with the broadest sense to include variations of the specific design and/or performance need described herein, as well as other variations that are well known to those of skill in the art. In particular, the shape and location of components and layers in the electrode assembly 500 may be adjusted or modified to meet specific design and/or performance needs. Furthermore, it is to be understood that other structures may have been omitted from the description of the electrode assembly 500 for clarity. The omitted structures may include, for example, sensor structures, insulating layers, interconnect components, passive devices, etc.

Figure 6:
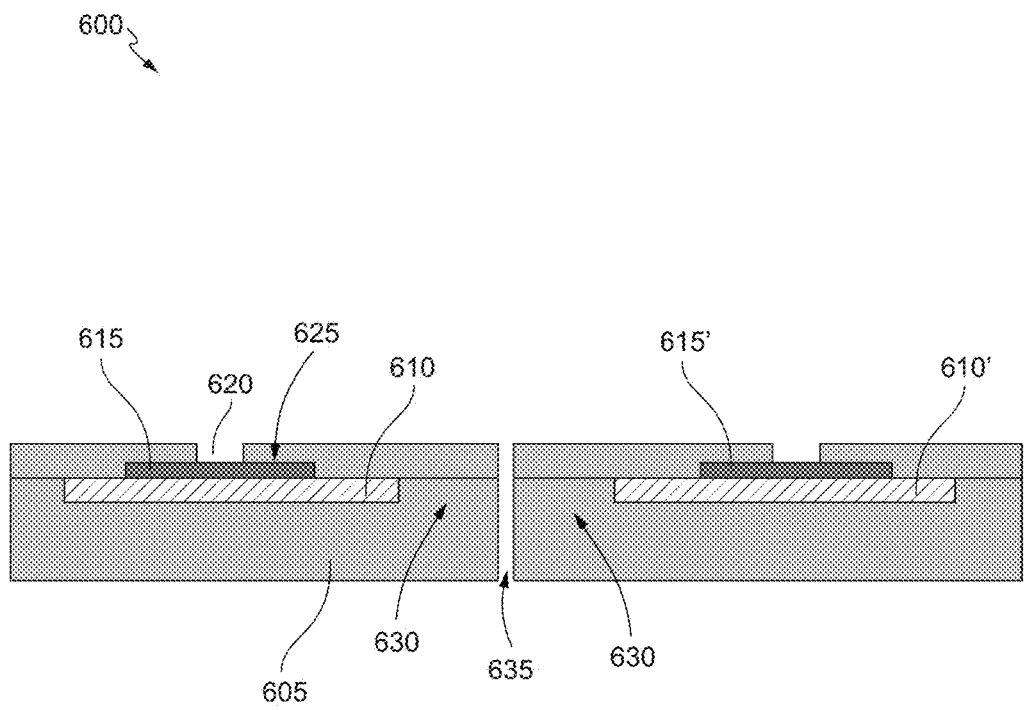
FIG. 6 shows a cross-sectional side view of a portion of an electrode assembly in accordance with some aspects of the present invention.

FIG. 6 shows a cross section of an electrode assembly 600 (e.g., as described with respect to FIG. 2, 3, or 4) fabricated in accordance with alternative aspects of the present invention. In various embodiments, the electrode assembly 600 may include an overmold 605 and a supporting structure 610 formed within a portion of the overmold 305, as similarly described with respect to FIG. 5. The electrode assembly 600 may further include one or more electronic structures (e.g., an electrode, wire, and/or bond/contact pad) that may be similar to that described with respect to FIG. 5, and thus the detailed description is not repeated. For example, the supporting structure 610 may be embedded within the overmold 605, and a metallization layer 615 (e.g., an electrode or wire) may be formed on a portion of the supporting structure 610. In some embodiments, the electrode assembly 600 may further include a trench 620 formed in the overmold 605 that exposes at least a portion of a top surface 625 of the metallization layer 615.

In some embodiments, the electrode assembly 600 may comprise one or more additional supporting structures that may support one or more additional electronic structures of the assembly such as an electrode, wire, and bond/contact pad. The supporting structures and electronic structures may be isolated from one another by region(s) 630 of the overmold 605 and/or spaces 635 (e.g., external environment). For example, as shown in FIG. 6, the electrode assembly 600 may further comprise one or more of supporting structure 610' and metallization layer 615'. The properties of the supporting structures and electronic structures (e.g., thickness, material, position, contact, etc.) may be the same or different from those of the structures previously discussed herein with reference to FIG. 5. However, it should be understood the electrode assembly 600 is an exemplary embodiment, and that the electrode assembly 600 is to be construed with the broadest sense to include variations of the specific design and/or performance need described herein, as well as other variations that are well known to those of skill in the art. In particular, the shape and location of components and layers in the electrode assembly 600 may be adjusted or modified to meet specific design and/or performance needs. Furthermore, it is to be understood that other structures may have been omitted from the description of the electrode assembly 600 for clarity. The omitted structures may include, for example, sensor structures, insulating layers, interconnect components, passive devices, etc.

Figure 7:
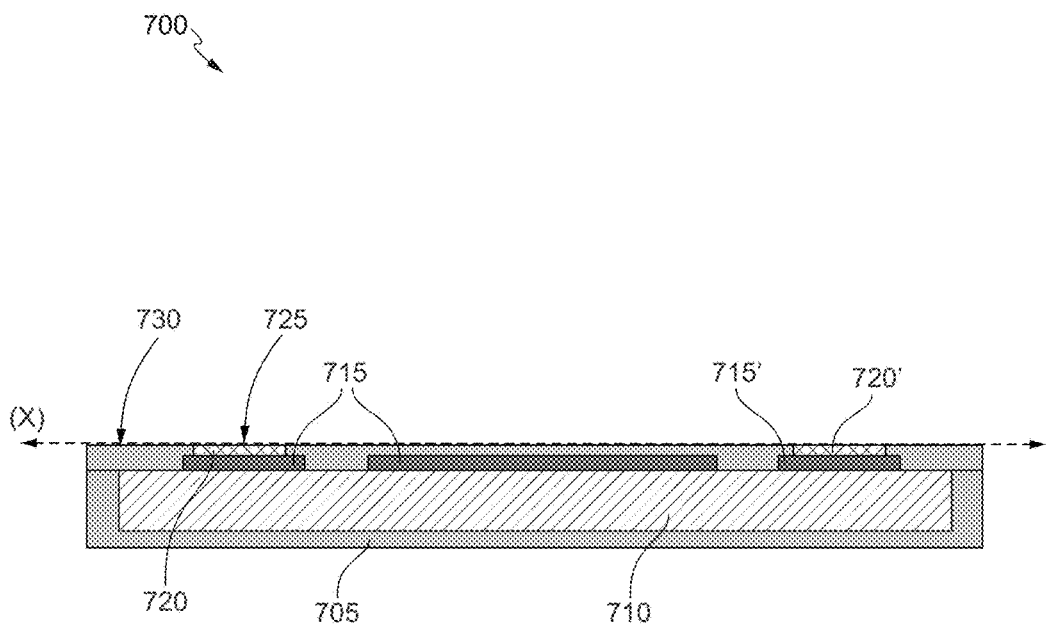
FIG. 7 shows a cross-sectional side view of a portion of an electrode assembly in accordance with some aspects of the present invention.

FIG. 7 shows a cross section of an electrode assembly 700 (e.g., as described with respect to FIG. 2, 3, or 4) fabricated in accordance with alternative aspects of the present invention. In various embodiments, the electrode assembly 700 may include an overmold 705 and a supporting structure 710 which may be formed within a portion of the overmold 705, as similarly described with respect to FIG. 5. The electrode assembly 700 may further include one or more electronic structures (e.g., an electrode, wire, and/or bond/contact pad) that may be similar to that described with respect to FIG. 5, and thus the detailed description is not repeated. For example, the supporting structure 710 may be embedded within the overmold 705, and one or more wiring layers 715 may be formed on a portion of the supporting structure 710. In some embodiments, the electrode assembly 700 may further include an electrode 720 formed on (e.g., indirectly) the supporting structure 710 and in electrical contact with one or more of the wiring layers 715. The electrode 720 may include a top surface 725 that is coplanar ("x") with the top surface 730 of the overmold 705 (shown in FIG. 7) or that is raised above the top surface 730 of the overmold 705 by a predetermined distance (shown for example in FIG. 5).

In some embodiments, the electrode assembly 700 may comprise one or more additional electronic structures such as an electrode, wire, and bond/contact pad on the supporting structure of the assembly. For example, as shown in FIG. 7, the electrode assembly 700 may further comprise one or more wiring layers 715' and an electrode 720'. The properties of the supporting structures and electronic structures (e.g., thickness, material, position, contact, etc.) may be the same or different from those of the structures previously discussed herein with reference to FIG. 5. However, it should be understood the electrode assembly 700 is an exemplary embodiment, and that the electrode assembly 700 is to be construed with the broadest sense to include variations of the specific design and/or performance need described herein, as well as other variations that are well known to those of skill in the art. In particular, the shape and location of components and layers in the electrode assembly 700 may be adjusted or modified to meet specific design and/or performance needs. Furthermore, it is to be understood that other structures may have been omitted from the description of the electrode assembly 700 for clarity. The omitted structures may, for example, include sensor structures, insulating layers, interconnect components, passive devices, etc.

III. Methods for Fabricating an Electrode Assembly

FIGS. 8A-8H show structures and respective processing steps for fabricating a thin-film electrode assembly 800 (e.g., as described with respect to FIG. 2, 3, 4, 5, 6, or 7) in accordance with various aspects of the invention. It should be understood by those of skill in the art that the thin-film electrode assembly can be manufactured in a number of ways using a number of different tools. In general, however, the methodologies and tools used to form the structures of the various embodiments can be adopted from integrated circuit (IC) technology. For example, the structures of the various embodiments, e.g., electrodes, wiring layers, bond/contact pads, etc., may be built on a substrate and realized in films of materials patterned by photolithographic processes. In particular, the fabrication of various structures described herein may typically use three basic building blocks: (i) deposition of films of material on a substrate and/or previous film(s), (ii) applying a patterned mask on top of the film(s) by photolithographic imaging, and (iii) etching the film(s) selectively to the mask.

As used herein, the term "depositing" may include any known or later developed techniques appropriate for the material to be deposited including but not limited to, for example: chemical vapor deposition (CVD), low-pressure CVD (LPCVD), plasma-enhanced CVD (PECVD), semi-atmosphere CVD (SACVD) and high density plasma CVD (HDPCVD), rapid thermal CVD (RTCVD), ultra-high vacuum CVD (UHVCVD), limited reaction processing CVD (LRPCVD), metalorganic CVD (MOCVD), sputtering deposition, ion beam deposition, electron beam deposition, laser assisted deposition, thermal oxidation, thermal nitridation, spin-on methods, physical vapor deposition (PVD), atomic layer deposition (ALD), chemical oxidation, molecular beam epitaxy (MBE), plating (e.g., electroplating), or evaporation.

Figure 8A:
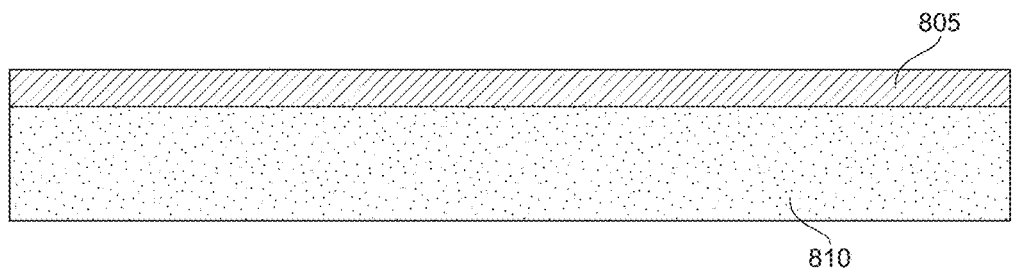
FIGS. 8A-8H show cross-sectional side views illustrating a method of forming an electrode assembly in accordance with some aspects of the present invention.

FIG. 8A shows a beginning structure comprising a first polymer layer 805 overlying a substrate 810 (e.g., a backer). The substrate 810 may be comprised of but not limited to silicon, germanium, silicon germanium, silicon carbide, and those materials consisting essentially of one or more Group III-V compound semiconductors having a composition defined by the formula $AlX1GaX2InX3AsY1PY2NY3SbY4$, where X1, X2, X3, Y1, Y2, Y3, and Y4 represent relative proportions, each greater than or equal to zero and $X1+X2+X3+Y1+Y2+Y3+Y4=1$ (1 being the total relative mole quantity). Substrate 810 may additionally or alternatively be comprised of Group II-VI compound semiconductors having a composition $ZnA1CdA2SeB1TeB2$, where A1, A2, B1, and B2 are relative proportions each greater than or equal to zero and $A1+A2+B1+B2=1$ (1 being a total mole quantity). The processes to provide, obtain, or fabricate substrate 810, as illustrated and described, are well known in the art and thus, no further description is provided herein.

The first polymer layer 805 may be comprised of an LCP or a thermoset polymer material, for example, a polymer of imide monomers (i.e., a polyimide). In some embodiments, the first polymer layer 805 may comprise an LCP or polyimide. In other embodiments, the first polymer layer 805 may comprise an epoxy, a polyester, a silicone, and/or a phenolic. The forming of the first polymer layer 805 may include depositing and curing a polymer material directly on the substrate 810 without an adhesion promoter. For example, a solution comprised of an imidizable polyamic acid compound dissolved in a vaporizable organic solvent without an adhesion promoter may be deposited (e.g., spin coated) onto the substrate 810. The solution may then be heated at a temperature, preferably less than 250° C., to imidize the polyamic acid compound to form the desired polyimide and vaporize the solvent. The first polymer layer 805 may then be thinned to a desired thickness by planarization, grinding, wet etch, dry etch, oxidation followed by oxide etch, or any combination thereof. This process can be repeated to achieve a desired thickness for the first polymer layer 805. In some embodiments, the first polymer layer 805 may have a thickness from 1.0 µm to 12.0 µm. In some embodiments, the first polymer layer 805 may have a thickness from 4.0 µm to 8.0 µm. In some embodiments, the first polymer layer 805 may have a thickness from 5.0 µm to 7.0 µm.

Figure 8B:
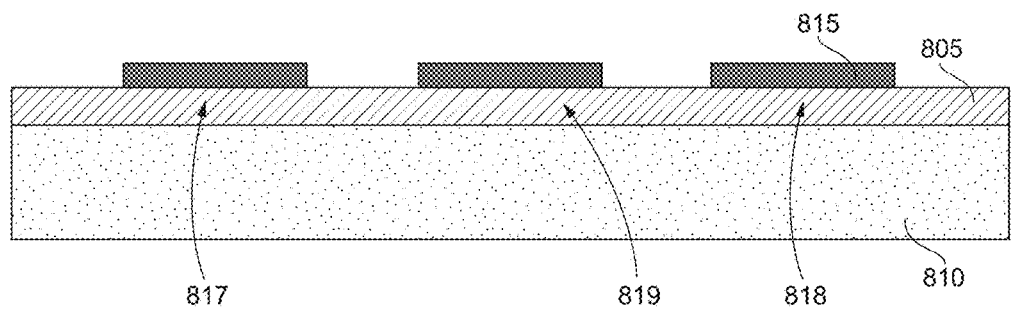

FIG. 8B shows a wiring layer 815 formed in a pattern over at least a portion (e.g., region(s)) of the first polymer layer 805. In some embodiments, forming the wiring layer 815 (e.g., a first metallization layer (M1)) may include depositing a seed layer (e.g., a copper (Cu) seed layer, a gold (Au) seed layer, a silver (Ag) seed layer, a gold/chromium (Au/Cr) seed layer, etc.) over the first polymer layer 805. The seed layer may be configured to enable forming of a wire on the first polymer layer 805 (e.g., through Cu electroplating, Au electroplating, Sn electroplating, Ag electroplating, Au/Cr electroplating, etc.). Optionally, and prior to forming of the seed layer, an adhesion layer may be deposited over the first polymer layer 805 to enable adequate application of the seed layer. Deposition of either or both of the adhesion layer and seed layer may include sputter deposition Following deposition of the seed layer, a resist pattern may be formed above the first polymer layer 805. The resist pattern may include openings that align over at least a portion of the first polymer layer 805 for forming of the wiring layer 815 (e.g., a wire with a cross-sectional thickness of about 0.5 µm to about 5 µm), and may be configured to enable forming of a wire on the first polymer layer 805. For example, the resist may be patterned with openings to form: (i) a first portion of the wiring layer 815 over a first region 817 of the first polymer layer 805, (ii) a second portion of the wiring layer 815 over a second region 818 of the first polymer layer 805, and (iii) a third portion of the wiring layer 815 over a third region 819 of the first polymer layer 805. In various embodiments, the openings of the resist pattern may have a serpentine pattern such that the formed wiring layer 815 has a serpentine shape, e.g. as shown in FIGS. 2A, 2B, and 2C. In other embodiments, the openings of the resist pattern may have a zig-zag or an accordion pattern such that the formed wiring layer 815 has a zig-zag or an accordion shape. It should be understood by those of skill in the art that different patterns are also contemplated by the present invention.

In various embodiments, the wiring layer 815 may be deposited through electroplating (e.g., through Cu electroplating, Au electroplating, Sn electroplating, Ag electroplating, Au/Cr electroplating, etc.) and may be positioned over at least a portion of the first polymer layer 805 (e.g., the first region 817, the second region 818, and the third region 819). The electroplating maybe performed at a current density of about 4.0 mA/cm2 to about 4.5 mA/cm2. In some embodiments, the exposed area or portion of the substrate may encompass about 8 cm2 to about 10 cm2. The current may be about 14 mA to about 18 mA and the duration may be from about 110 minutes to about 135 minutes to form the wiring layer 815 having a thickness of about 8 µm to about 10 µm. In other embodiments, the exposed area or portion of the substrate may encompass about 10 cm2 to about 18 cm2. The current may be about 18 mA to about 28 mA and the duration may be from about 35 minutes to about 50 minutes to form the wiring layer 815 having a thickness of about 2 µm to about 5 µm.

Following the deposition of the wiring layer 815, the intermediate structure may be subjected to a strip resist to remove the resist pattern and expose portions of the seed layer (portions without wire formation), and optionally the adhesion layer. The exposed portions of the seed layer, and optionally the adhesion layer, may then be subjected to an etch (e.g., wet etch, dry etch, etc.) to remove those portions, thereby isolating the wiring layer 815 over at least a portion of the first polymer layer 805.

Figure 8C:
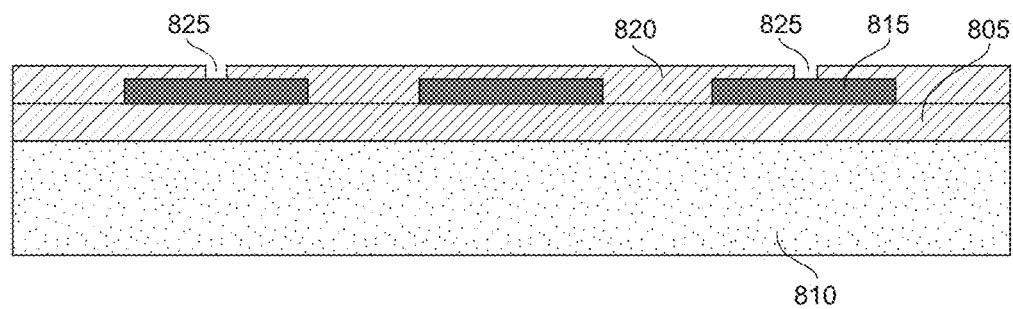

FIG. 8C shows a second polymer layer 820 formed over the wiring layer 815 and the first polymer layer 805, and contact vias 825 formed in the second polymer layer 820 to expose at least a portion of the top surface the wiring layer 815. The second polymer layer 820 may be comprised of an LCP or thermoset polymer material, for example, a polymer of imide monomers (i.e., a polyimide). In some embodiments, the second polymer layer 820 comprises an LCP or polyimide. In other embodiments, the second polymer layer 820 comprises an epoxy, a polyester, a silicone, and/or a phenolic. The second polymer layer 820 may be comprised of the same material or a different material from that of the first polymer layer 805.

The forming of the second polymer layer 820 may include depositing and curing of a polymer material directly on the wiring layer 815 and the first polymer layer 805. For example, a solution comprised of an imidizable polyamic acid compound dissolved in a vaporizable organic solvent may be applied to the wiring layer 815 and the first polymer layer 805. The solution may then be heated at a temperature, preferably less than 250° C., to imidize the polyamic acid compound to form the desired polyimide and vaporize the solvent. The second polymer layer 820 may then be thinned to a desired thickness by planarization, grinding, wet etch, dry etch, oxidation followed by oxide etch, or any combination thereof. This process can be repeated to achieve a desired thickness for the second polymer layer 820. In some embodiments, the second polymer layer 820 may have a thickness from 1.0 µm to 12.0 µm. In some embodiments, the second polymer layer 820 may have a thickness from 4.0 µm to 8.0 µm. In some embodiments, the second polymer layer 820 may have a thickness from 5.0 µm to 7.0 µm.

In various embodiments, the contact vias 825 may be formed in the second polymer layer 820 to the underlying wiring layer 815. The contact vias 825 can e.g. be formed using conventional lithographic, etching, and cleaning processes, known to those of skill in the art.

Figure 8D:
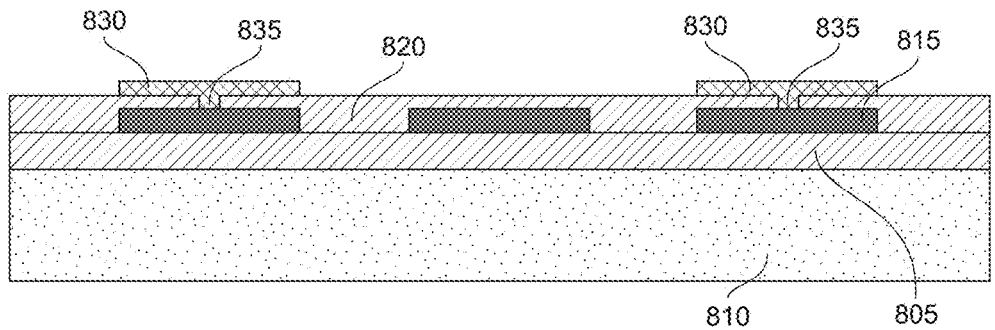

FIG. 8D shows electrodes 830 and contacts 835 (e.g., second metallization layer (M2)) formed on and within the contact vias 825 to the portion of the top surface the wiring layer 815. In various embodiments, the electrodes 830 and contacts 835 may be formed using conventional processes. For example, a conductive material may be blanket deposited on the second polymer layer 820, including within the contact vias 825 and in contact with the portion of the top surface the wiring layer 815. The conductive material may be copper (Cu), gold (Au), silver (Ag), titanium (Ti), or platinum (Pt), or alloys thereof such as gold/chromium (Au/Cr) or Titanium/Platinum (Ti/Pt), for example. Once the conductive material is deposited, the conductive material may be patterned using conventional lithography and etching processes to form at least one electrode 830 or a pattern of electrodes 830 as shown in FIG. 8D, for example. In some embodiments, the pattern of electrodes 830 may include each electrode 830 spaced apart from one another via a portion or region 840 of the second polymer layer 820 that does include the wiring layer 815 but does not include electrodes 830. It should be understood by those of skill in the art that different patterns are also contemplated by the present invention.

Figure 8E:
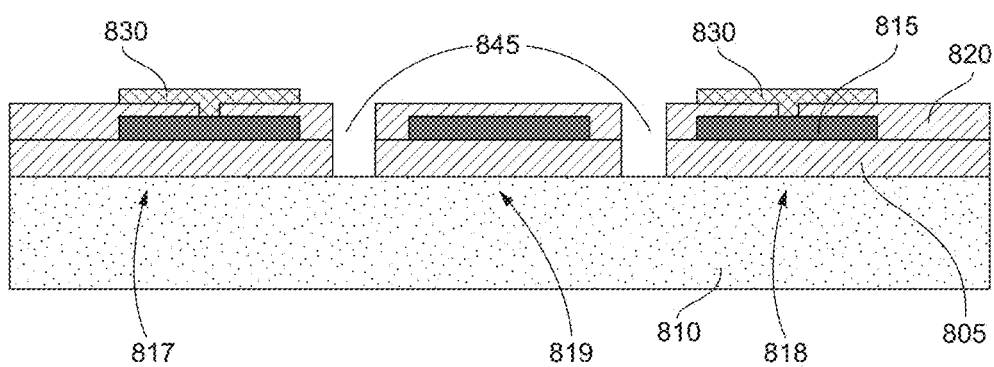

FIG. 8E shows trenches 845 formed within the first polymer layer 805 and the second polymer layer 820 to separate the first polymer layer 805 and the second polymer layer 820 into regions 817, 818, 819. In various embodiments, the trenches 845 may be formed in the first polymer layer 805 and the second polymer layer 820. These trenches 845 may extend to the underlying substrate 810. The first region 817 and the second region 818 may be separated from one another by the third region 819 that does include at least a portion of the wiring layer 815 but does not include an electrode. The trenches 845 can be patterned using conventional lithographic, etching, and cleaning processes, to form the pattern of trenches 845 shown in FIG. 8E, for example. Is some embodiments, the photoresist used to etch the trench patterns has a thickness of greater than 30 µm such that the first polymer layer 805 and the second polymer layer 820 can be etched effectively.

Figure 8F:
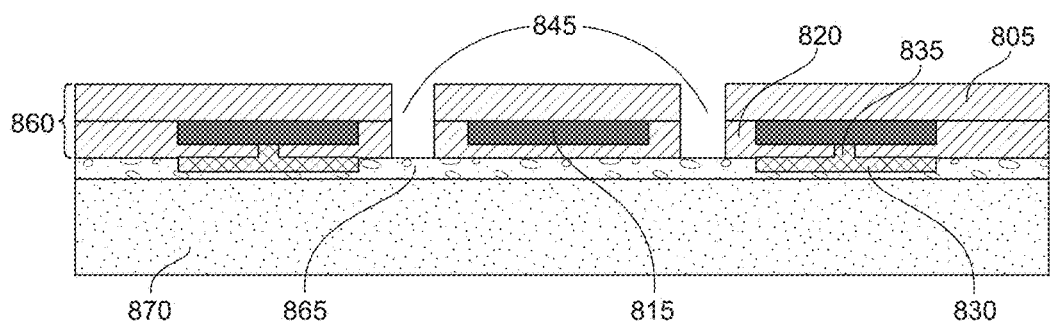

FIG. 8F shows an intermediate structure 860 of the thin-film electrode assembly 800 including the first polymer layer 805, the wiring layer 815, the second polymer layer 820, the electrodes 830, the contacts 835, and the trenches 845 detached from the substrate 810, and flipped upside down such that at least top surfaces of the electrodes 830 are temporarily bonded to an adhesive layer 865 formed on a surface of a substrate 870. The substrate 870 may be the substrate 810 reused with an adhesive layer 865 deposited thereon, or the substrate 870 may be a completely different substrate made of similar or different material to that included with the substrate 810. For example, in some embodiments, the substrate 870 may be a completely different substrate comprised of but not limited to silicon, germanium, silicon germanium, silicon carbide, and those materials consisting essentially of one or more Group III-V compound semiconductors having a composition defined by the formula $Al_{X1}Ga_{X2}In_{X3}As_{Y1}P_{Y2}N_{Y3}Sb_{Y4}$, where X1, X2, X3, Y1, Y2, Y3, and Y4 represent relative proportions, each greater than or equal to zero and X1+X2+X3+Y1+Y2+Y3+Y4=1 (1 being the total relative mole quantity). Substrate 870 may additionally or alternatively be comprised of Group II-VI compound semiconductors having a composition $Zn_{A1}Cd_{A2}Se_{B1}Te_{B2}$, where A1, A2, B1, and B2 are relative proportions each greater than or equal to zero and A1+A2+B1+B2=1 (1 being a total mole quantity). The processes to provide, obtain, or fabricate substrate 865, as illustrated and described, are well known in the art and thus, no further description is provided herein.

The adhesive layer 865 may be comprised of a thermoplastic temporary mounting adhesive, for example, a wash away adhesive such as Crystalbond™, Wafer-Mount™, or QuickStick™. In some embodiments, the forming of the intermediate structure 860 flipped upside down on the adhesive layer 865 and the substrate 870 may include detaching the intermediate structure 860 from the substrate 810, mixing a thermoplastic temporary mounting adhesive in a solution, depositing (e.g., spraying) the solution on a top surface of the substrate 870, heating the solution to evaporate the solvents and form the adhesive layer 865, pressing the upside down intermediate structure 860 into the adhesive layer 865 such that at least top surfaces of the electrodes 830 are in directed contact with the adhesive layer 865, and cooling at room temperature until the adhesive layer 865 is completely dry and the intermediate structure 860 is temporarily bonded to the substrate 870. In alternative embodiments, the forming of the intermediate structure 860 flipped upside down on the adhesive layer 865 and the substrate 870 may include detaching the intermediate structure 860 from the substrate 810, heating a thermoplastic temporary mounting adhesive to a flow temperature, depositing (e.g., use of a mounting block) the adhesive on a top surface of the substrate 870 to form the adhesive layer 865, pressing the upside down intermediate structure 860 into the adhesive layer 865 such that at least top surfaces of the electrodes 830 are in directed contact with the adhesive layer 865, and cooling at room temperature until the adhesive layer 865 is completely dry, and the intermediate structure 860 and the substrate 870 are temporarily bonded to the substrate 870.

Figure 8G:
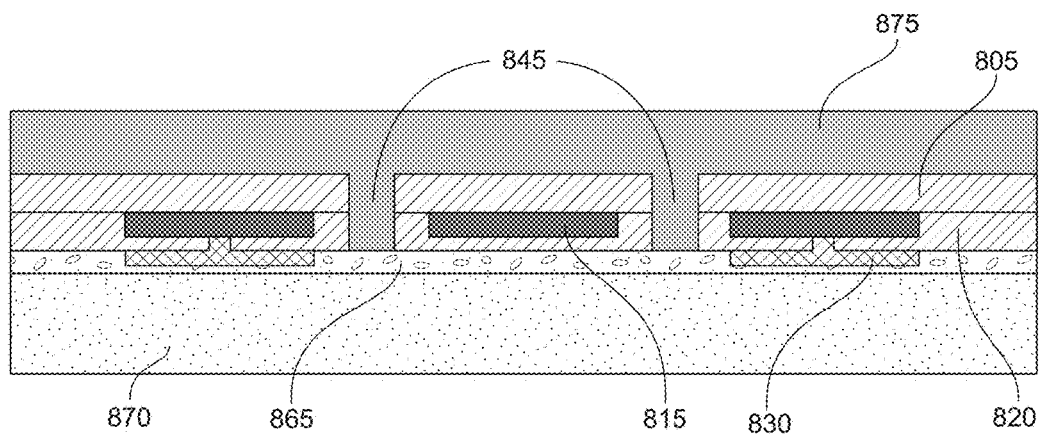

FIG. 8G shows a third polymer layer 875 formed over the first polymer layer 805 and the trenches 845 formed in the first polymer layer 805 and the second polymer layer 820 to the underlying adhesive layer 865. The third polymer layer 875 may be comprised of a medical grade polymer material, for example, a soft polymer such as silicone or a polymer dispersion such as latex. In some embodiments, the third polymer layer 875 may comprise silicone. In other embodiments, the third polymer layer 875 may comprise latex, silicone, polytetrafluoroethylene (PTFE), perfluoroether (PFA), fluorinated ethylene propylene (FEP), polylactic acid (PLA), polyglycolic acid (PGA), polycaprolactone (PCL), polyether ether ketone (PEEK), and/or ethylene vinyl acetate (EVA).

The forming of the third polymer layer 875 may include depositing and curing of a polymer material directly on a bottom surface of the first polymer layer 805 and the trenches 845 formed in the first polymer layer 805 and the second polymer layer 820 to the underlying adhesive layer 865. For example, a solution comprised of polysiloxanes dissolved in a vaporizable organic solvent may be applied to a bottom surface of the first polymer layer 805 and the trenches 845 may formed in the first polymer layer 805 and the second polymer layer 820, e.g. to extend to the underlying adhesive layer 865. The solution may then be heated at a temperature, preferably less than 250° C., to cure the polysiloxanes to form the desired silicone and vaporize the solvent. A surface of the third polymer layer 875 within the trenches 845 may be coplanar with a top surface of the second polymer layer 820. The third polymer layer 875 may then be thinned to a desired thickness by planarization, grinding, wet etch, dry etch, oxidation followed by oxide etch, or any combination thereof. This process can be repeated to achieve a desired thickness for the third polymer layer 875. The third polymer layer 875 may be plasma treated such that it forms a covalent bond to the first polymer layer 805 and/or the second polymer layer 820 to prevent separation of the materials and provide a moisture barrier. In some embodiments, the third polymer layer 875 may have a thickness from 100.0 µm to 500.0 µm. In some embodiments, the third polymer layer 875 may have a thickness from 200.0 µm to 400.0 µm. In some embodiments, the third polymer layer 875 may have a thickness from 250.0 µm to 350.0 µm.

Figure 8H:
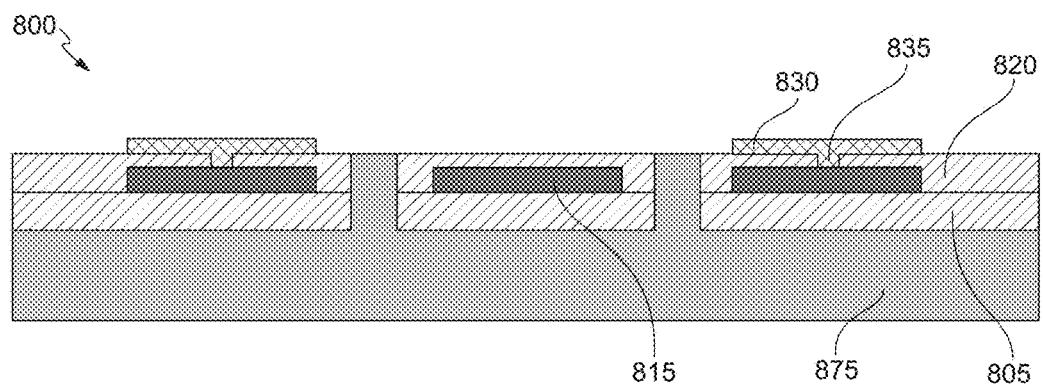

FIG. 8H shows the thin-film electrode assembly 800 including the first polymer layer 805, the wiring layer 815, the second polymer layer 820, the electrodes 830, the contacts 835, and the third polymer layer 875 detached from the adhesive layer 865 and the substrate 870, and flipped topside up. In some embodiments, detaching the thin-film electrode assembly 800 from the adhesive layer 865 and the substrate 870 may include removal of the adhesive (e.g., applying a stripper solution to dissolve the adhesive), and cleaning (e.g., a step-wise rinsing process) at least top surfaces of the electrodes 830 and the second polymer layer 820 with acetone, isopropyl alcohol, non-ionic surfactant, a liquid detergent system, and/or deionized water to remove residual material such as remaining adhesive material.

FIGS. 9A-9H show structures and respective processing steps for fabricating an alternative thin-film electrode assembly 900 (e.g., a neural probe) in accordance with various aspects of the invention. It should be understood by those of skill in the art that the thin-film electrode assembly can be manufactured in a number of ways using a number of different tools. In general, however, the methodologies and tools used to form the structures of the various embodiments can be adopted from integrated circuit (IC) technology. For example, the structures of the various embodiments, e.g., electrodes, wiring layers, bond/contact pads, etc., may be built on a substrate and are realized in films of materials patterned by photolithographic processes. In particular, the fabrication of various structures described herein may typically use three basic building blocks: (i) deposition of films of material on a substrate and/or previous film(s), (ii) applying a patterned mask on top of the film(s) by photolithographic imaging, and (iii) etching the film(s) selectively to the mask.

Figure 9A:
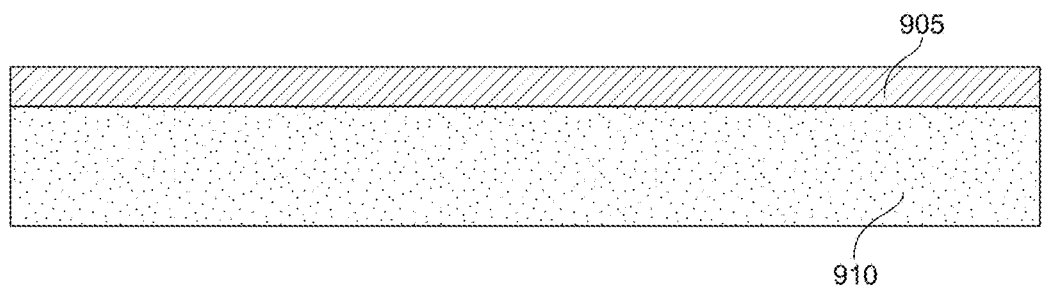
FIGS. 9A-9H show cross-sectional side views illustrating an alternative method of forming an electrode assembly in accordance with some aspects of the present invention.

FIG. 9A shows a beginning structure comprising a first polymer layer 905 overlying a substrate 910 (e.g., a backer). The substrate 910 may be comprised of but not limited to silicon, germanium, silicon germanium, silicon carbide, and those materials may consist essentially of one or more Group III-V compound semiconductors having a composition defined by the formula AlX1GaX2InX3AsY1PY2NY3SbY4, where X1, X2, X3, Y1, Y2, Y3, and Y4 represent relative proportions, each greater than or equal to zero and X1+X2+X3+Y1+Y2+Y3+Y4=1 (1 being the total relative mole quantity). Substrate 910 may additionally or alternatively be comprised of Group II-VI compound semiconductors having a composition ZnA1CdA2SeB1TeB2, where A1, A2, B1, and B2 are relative proportions each greater than or equal to zero and A1+A2+B1+B2=1 (1 being a total mole quantity). The processes to provide, obtain, or fabricate substrate 910, as illustrated and described, are well known in the art and thus, no further description is provided herein.

The first polymer layer 905 may be comprised of an LCP or a thermoset polymer material, for example, a polymer of imide monomers (i.e., a polyimide). In some embodiments, the first polymer layer 905 may comprise an LCP or polyimide. In other embodiments, the first polymer layer 905 may comprise an epoxy, a polyester, a silicone, and/or a phenolic. The forming of the first polymer layer 905 may include depositing and curing a polymer material directly on the substrate 910 without an adhesion promoter. For example, a solution comprised of an imidizable polyamic acid compound dissolved in a vaporizable organic solvent without an adhesion promoter may be deposited (e.g., spin coated) onto the substrate 910. The solution may then be heated at a temperature, preferably less than 250° C., to imidize the polyamic acid compound to form the desired polyimide and vaporize the solvent. The first polymer layer 905 may then be thinned to a desired thickness by planarization, grinding, wet etch, dry etch, oxidation followed by oxide etch, or any combination thereof. This process can be repeated to achieve a desired thickness for the first polymer layer 905. In some embodiments, the first polymer layer 905 may have a thickness from 1.0 μm to 12.0 μm. In some embodiments, the first polymer layer 905 may have a thickness from 4.0 μm to 8.0 μm. In some embodiments, the first polymer layer 905 may have a thickness from 5.0 μm to 7.0 μm.

Figure 9B:
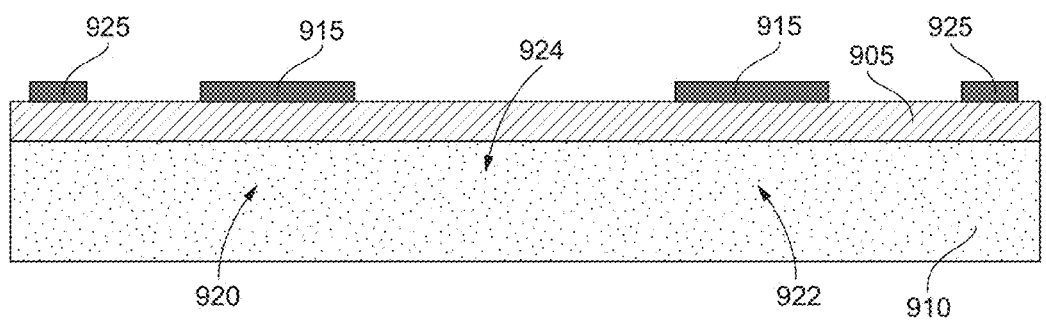

FIG. 9B shows wiring layer 915 (e.g., metallization layer (M1)) formed on the first polymer layer 905. In various embodiments, the wiring layer 915 may include electrode(s) and/or wiring, and may be formed using conventional processes. For example, a conductive material may be blanket deposited on the first polymer layer 905. The conductive material may be copper (Cu), gold (Au), silver (Ag), titanium (Ti), or platinum (Pt), or alloys thereof such as gold/chromium (Au/Cr) or Titanium/Platinum (Ti/Pt), for example. Once the conductive material is deposited, the conductive material may be patterned using conventional lithography and etching processes to form a pattern of the wiring layer 915. In some embodiments, the pattern of the wiring layer 915 may include each portion of the wiring layer 915 (e.g., a wire or electrode) spaced apart from one another via a portion or region of the first polymer layer 905 that does not include wiring or conductive material. For example, the conductive material may be patterned to form: (i) a first portion of the wiring layer 915 over a first region 920 of the first polymer layer 905, and (ii) a second portion of the wiring layer 915 over a second region 922 of the first polymer layer 905. The first region 920 and the second region 922 of the first polymer layer 905 may be separated from one another by the third region 924 of the first polymer layer 905 that does not include the wiring layer 915. It should be understood by those of skill in the art that different patterns are also contemplated by the present invention.

In some embodiments, an etch stop layer 925 may be deposited on the outside of pattern of the wiring layer 915 (shown) and/or under the pattern of the wiring layer 915 (not shown). The etch stop layer 925 may be comprised of a material featuring drastically different etch characteristics (e.g., on a oxide of a metalloid such as silicon oxide, an oxide of a metal, a nitride of a metal, a carbide of a metal, or a combination thereof) than the material to be etched to stop the etching process. The etch stop layer 925 may be used to stop etching of the polymer layer 905 after further processing as discussed herein with respect to FIG. 9E.

Figure 9C:
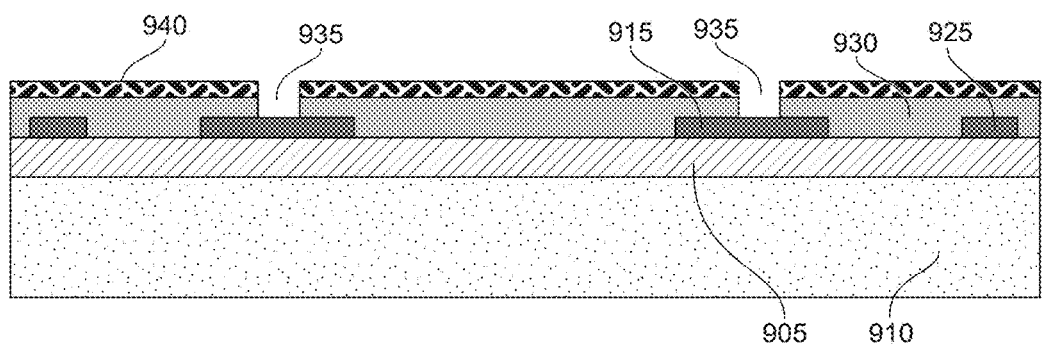

FIG. 9C shows a second polymer layer 930 formed over the first polymer layer 905 and the wiring layer 915, and trenches 935 formed within the second polymer layer 930 to expose a at least a portion of a top surface of the wiring layer 915. The second polymer layer 930 may be comprised of a medical grade polymer material, for example, a soft polymer such as silicone or a polymer dispersion such as latex. In some embodiments, the second polymer layer 930 may comprise silicone. In other embodiments, the second polymer layer 930 may comprise latex, silicone, polytetrafluoroethylene (PTFE), perfluoroether (PFA), fluorinated ethylene propylene (FEP), polylactic acid (PLA), polyglycolic acid (PGA), polycaprolactone (PCL), polyether ether ketone (PEEK), and/or ethylene vinyl acetate (EVA).

The forming of the second polymer layer 930 may include depositing and curing of a polymer material directly on the first polymer layer 905 and the wiring layer 915. For example, a solution comprised of polysiloxanes dissolved in a vaporizable organic solvent may be applied to the first polymer layer 905 and the wiring layer 915. The solution may then be heated at a temperature, preferably less than 250° C., to cure the polysiloxanes to form the desired silicone and vaporize the solvent. The second polymer layer 930 may then be thinned to a desired thickness by planarization, grinding, wet etch, dry etch, oxidation followed by oxide etch, or any combination thereof. This process can be repeated to achieve a desired thickness for the second polymer layer 930. The second polymer layer 930 may be plasma treated such that it forms a covalent bond to the first polymer layer 905 to prevent separation of the materials and provide a moisture barrier. In some embodiments, the second polymer layer 930 may have a thickness from 2.0 μm to 40.0 μm. In some embodiments, the second polymer layer 930 may have a thickness from 5.0 μm to 25.0 μm. In some embodiments, the second polymer layer 930 may have a thickness from 10.0 μm to 20.0 μm.

In various embodiments, the trenches 935 may be formed in the second polymer layer 930 to expose at least a portion of a top surface of the wiring layer 915. The trenches 935 can be patterned using conventional lithographic, etching, and cleaning processes, to form the pattern of trenches 935 shown in FIG. 9C, for example. For example, the trenches 935 may be formed into the second polymer layer 930 over the first portion of the wiring layer 915 and the second portion of the wiring layer 915 to expose at least a portion of a top surface of the wiring layer 915. In some embodiments, a mask 940 may be used to etch the trench patterns. Such a mask may comprise a metal layer such as copper (Cu), gold (Au), silver (Ag), titanium (Ti), or platinum (Pt), or alloys thereof such as gold/chromium (Au/Cr) or Titanium/Platinum (Ti/Pt), and the second polymer layer 930 may be etched using a plasma dry etch. The mask 940 may be left over the second polymer layer 930 for further processing, as described herein.

Figure 9D:
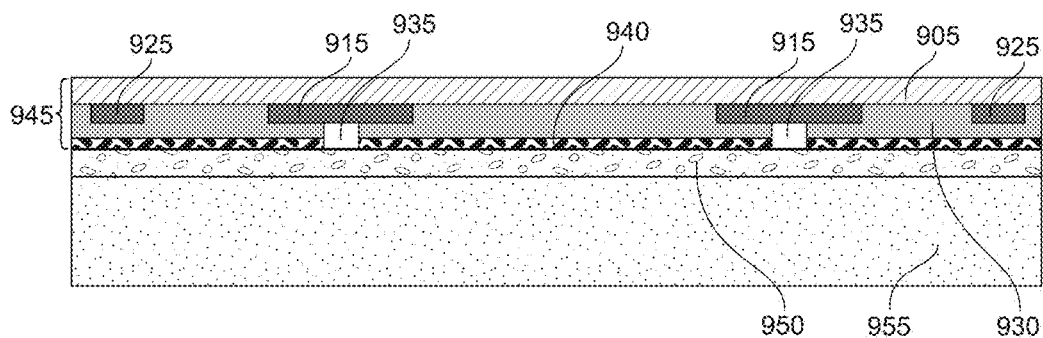

FIG. 9D shows an intermediate structure 945 of the thin-film electrode assembly 900 including the first polymer layer 905, the wiring layer 915, the etch stop layer 925, the second polymer layer 930, the trenches 935, and the mask 940 detached from the substrate 910, and flipped upside down such that at least a top surface of the intermediate structure or mask 940 is temporarily bonded to an adhesive layer 950 formed on a surface of a substrate 955. The substrate 955 may be the substrate 910 reused with an adhesive layer 950 deposited thereon, or the substrate 955 may be a completely different substrate made of similar or different material to that included with the substrate 910. For example, in some embodiments, the substrate 955 may be a completely different substrate comprised of but not limited to silicon, germanium, silicon germanium, silicon carbide, and those materials consisting essentially of one or more Group III-V compound semiconductors having a composition defined by the formula $Al_{X1}Ga_{X2}In_{X3}As_{Y1}P_{Y2}N_{Y3}Sb_{Y4}$, where X1, X2, X3, Y1, Y2, Y3, and Y4 represent relative proportions, each greater than or equal to zero and $X1+X2+X3+Y1+Y2+Y3+Y4=1$ (1 being the total relative mole quantity). Substrate 955 may additionally or alternatively be comprised of Group II-VI compound semiconductors having a composition $Zn_{A1}Cd_{A2}Se_{B1}Te_{B2}$, where A1, A2, B1, and B2 are relative proportions each greater than or equal to zero and $A1+A2+B1+B2=1$ (1 being a total mole quantity). The processes to provide, obtain, or fabricate substrate 955, as illustrated and described, are well known in the art and thus, no further description is provided herein.

The adhesive layer 950 may be comprised of a temporary mounting adhesive, for example, a heat release tape that behaves like normal adhesive tape at room temperature but can be easily peeled off by heating when the tape is to be remove (e.g., REVALPHA®). In some embodiments, the forming of the intermediate structure 945 flipped upside down on the adhesive layer 950 and the substrate 955 may include laminating the release side of the temporary mounting adhesive tape onto a top surface of the mask 940, peeling off the intermediate structure 945 from the substrate 910, and laminating the adhesive side of the temporary mounting adhesive tape onto a top surface of the substrate 955 such that the intermediate structure 945 is temporarily bonded to the substrate 955.

Figure 9E:
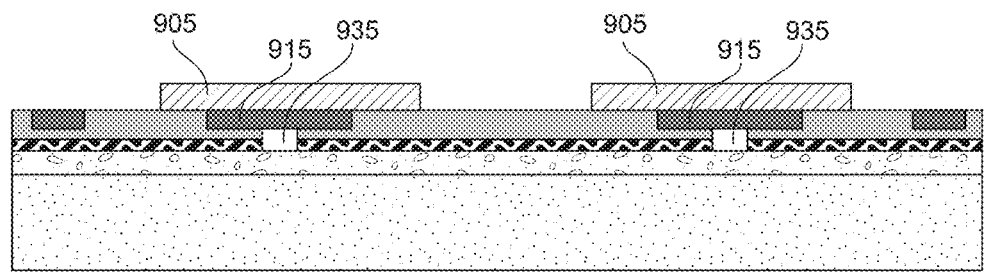

FIG. 9E shows patterning of the first polymer layer 905. In various embodiments, conventional lithographic, etching, and cleaning processes may be used to form the pattern of the first polymer layer 905 shown in FIG. 9E, for example. Is some embodiments, a mask may be used to etch the patterns. Such a mask may comprise a metal layer such as copper (Cu), gold (Au), silver (Ag), titanium (Ti), or platinum (Pt), or alloys thereof such as gold/chromium (Au/Cr) or Titanium/Platinum (Ti/Pt), and the first polymer layer 905 may be etched using a plasma dry etch to the etch stop layer 925. The mask may then be removed. The first polymer layer 905 may be etched into separate regions aligned with the wiring layer 915 and/or trenches 935 to provide support for the wiring layer 915.

Figure 9F:
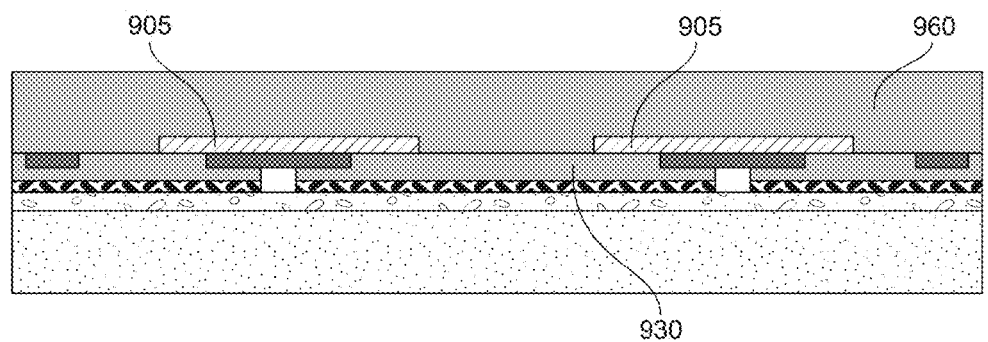

FIG. 9F shows a third polymer layer 960 formed over the first polymer layer 905 and the second polymer layer 930. The third polymer layer 960 may be comprised of a medical grade polymer material, for example, a soft polymer such as silicone or a polymer dispersion such as latex. In some embodiments, the third polymer layer 960 may comprise silicone. In other embodiments, the third polymer layer 960 may comprise latex, silicone, polytetrafluoroethylene (PTFE), perfluoroether (PFA), fluorinated ethylene propylene (FEP), polylactic acid (PLA), polyglycolic acid (PGA), polycaprolactone (PCL), polyether ether ketone (PEEK), and/or ethylene vinyl acetate (EVA). The third polymer layer 960 may be comprised of the same material or a different material from that of the second polymer layer 930.

The forming of the third polymer layer 960 includes depositing and curing of a polymer material directly on the first polymer layer 905 and the second polymer layer 930. For example, a solution comprised of polysiloxanes dissolved in a vaporizable organic solvent may be applied to the first polymer layer 905 and the second polymer layer 930. The solution may then be heated at a temperature, preferably less than 250° C., to cure the polysiloxanes to form the desired silicone and vaporize the solvent. The third polymer layer 960 may then be thinned to a desired thickness by planarization, grinding, wet etch, dry etch, oxidation followed by oxide etch, or any combination thereof. This process can be repeated to achieve a desired thickness for the third polymer layer 960. The third polymer layer 960 may be plasma treated such that it forms a covalent bond to the first polymer layer 905 and/or the second polymer layer 930 to prevent separation of the materials and provide a moisture barrier. In some embodiments, the third polymer layer 960 may have a thickness from 100.0 μm to 500.0 μm. In some embodiments, the third polymer layer 960 may have a thickness from 200.0 μm to 400.0 μm. In some embodiments, the third polymer layer 960 may have a thickness from 250.0 μm to 350.0 μm.

Figure 9G:
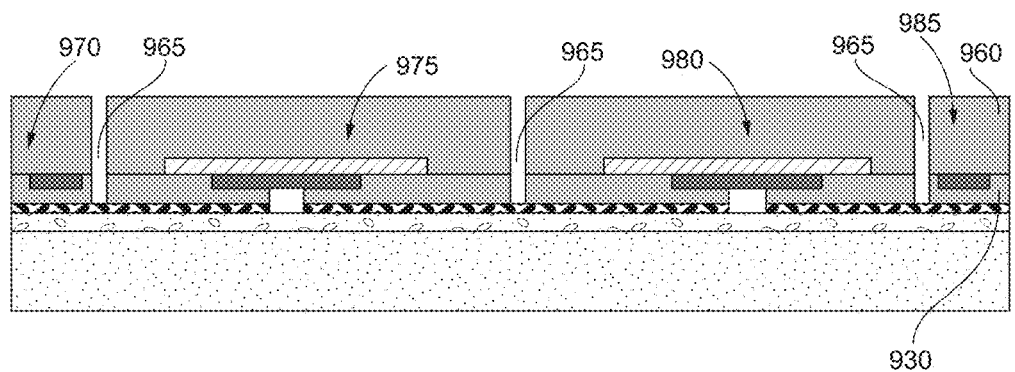

FIG. 9G shows trenches 965 formed within the second polymer layer 930 and the third polymer layer 960 to separate the second polymer layer 930 and the third polymer layer 960 into portions or regions 970, 975, 980, 985. In various embodiments, the trenches 965 may be formed in the second polymer layer 930 and the third polymer layer 960 to the underlying mask 940. In some embodiments, the trenches 965 can be patterned using conventional lithographic, etching, and cleaning processes, to form the pattern of trenches 965 shown in FIG. 9G, for example. In other embodiments, the trenches 965 can be patterned using conventional laser cutting processes, to form the pattern of trenches 965 shown in FIG. 9G, for example.

Figure 9H:
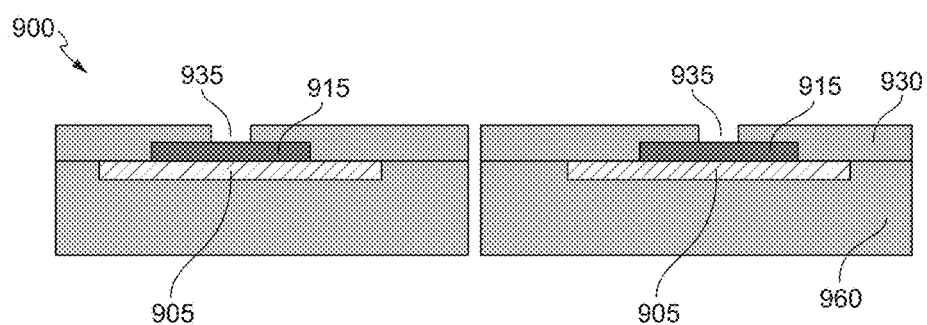

In FIG. 9H shows the thin-film electrode assembly 900 including the first polymer layer 905, the wiring layer 915, the second polymer layer 930, the trenches 935, and the third polymer layer 960 detached from the adhesive layer 950 and the substrate 955, and flipped topside up. In some embodiments, detaching the thin-film electrode assembly 300 from the adhesive layer 950 and the substrate 955 may include removal of the adhesive (e.g., heating the heat release tape), and cleaning (e.g., a step-wise rinsing process) at least top surfaces of the wiring layer 915 and the second polymer layer 930 with acetone, isopropyl alcohol, non-ionic surfactant, a liquid detergent system, and/or deionized water to remove residual material such as remaining adhesive material.

FIGS. 10A-10F show structures and respective processing steps for fabricating an alternative thin-film electrode assembly 1000 (e.g., as described with respect to FIG. 2, 3, 4, 5, 6, or 7) in accordance with various aspects of the invention. It should be understood by those of skill in the art that the thin-film electrode assembly can be manufactured in a number of ways using a number of different tools. In general, however, the methodologies and tools used to form the structures of the various embodiments can be adopted from integrated circuit (IC) technology. For example, the structures of the various embodiments, e.g., electrodes, wiring layers, bond/contact pads, etc., may be built on a substrate and are realized in films of materials patterned by photolithographic processes. In particular, the fabrication of various structures described herein may typically use three basic building blocks: (i) deposition of films of material on a substrate and/or previous film(s), (ii) applying a patterned mask on top of the film(s) by photolithographic imaging, and (iii) etching the film(s) selectively to the mask.

Figure 10A:
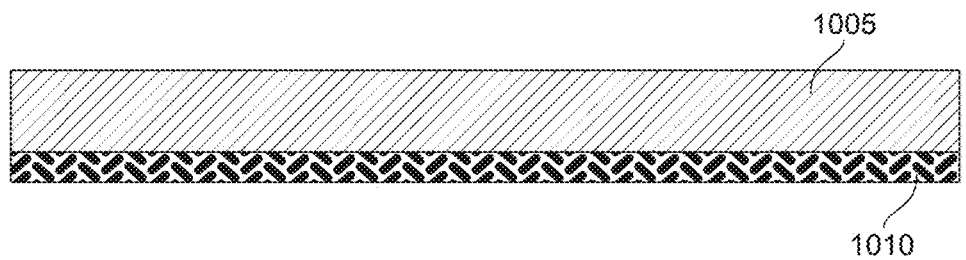
FIGS. 10A-10F show cross-sectional side views illustrating an alternative method of forming an electrode assembly in accordance with some aspects of the present invention.

FIG. 10A shows a beginning structure comprising a first polymer layer 1005 overlying a substrate 1010. In some embodiments, the first polymer layer 1005 may comprise an LCP or a thermoset polymer material, for example, a polymer of imide monomers (i.e., a polyimide). In other embodiments, the first polymer layer 1005 may comprise an epoxy, a polyester, a silicone, and/or a phenolic. The substrate 1010 may be comprised of silicon, copper (Cu), gold (Au), silver (Ag), titanium (Ti), or platinum (Pt), or alloys thereof such as gold/chromium (Au/Cr) or Titanium/Platinum (Ti/Pt), for example. In various embodiments, a layer of the substrate 1010 may be initially provided overlying the first polymer layer 1005 and may be subsequently stripped off of the polymer layer 1005 to form the beginning structure shown in FIG. 10A. The processes to provide, obtain, or fabricate the beginning structure, as illustrated and described, are well known in the art and thus, no further description is provided herein.

Figure 10B:
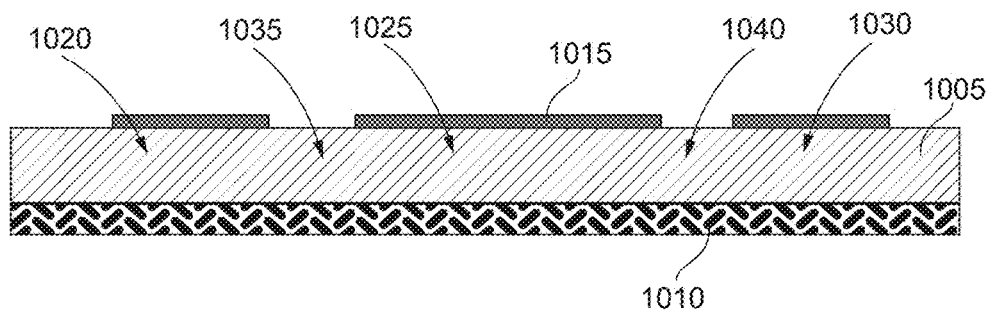

FIG. 10B shows wiring layer 1015 (e.g., metallization layer (M1)) formed on the first polymer layer 1005. In various embodiments, the wiring layer 1015 may include electrode(s) and/or wiring, and may be formed using conventional processes. For example, a conductive material maybe blanket deposited on the first polymer layer 1005. The conductive material may be copper (Cu), gold (Au), silver (Ag), titanium (Ti), or platinum (Pt), or alloys thereof such as gold/chromium (Au/Cr) or Titanium/Platinum (Ti/Pt), for example. Once the conductive material is deposited, the conductive material may be patterned using conventional lithography and etching processes to form a pattern of the wiring layer 1015. In some embodiments, the pattern of the wiring layer 1015 may include each portion of the wiring layer 1015 (e.g., a wire or electrode) spaced apart from one another via a portion or region of the first polymer layer 1005 that does not include wiring or conductive material. For example, the conductive material may be patterned to form: (i) a first portion of the wiring layer 1015 over a first region 1020 of the first polymer layer 1005, (ii) a second portion of the wiring layer 1015 over a second region 1025 of the first polymer layer 1005, and (iii) a third portion of the wiring layer 1015 over a third region 1030 of the first polymer layer 1005. The first region 1020, the second region 1025, and the third region 1030 of the first polymer layer 1005 may be separated from one another by a fourth region 1035 and fifth region 1040, respectively, of the first polymer layer 1005 that does not include the wiring layer 1015. It should be understood by those of skill in the art that different patterns are also contemplated by the present invention.

Figure 10C:
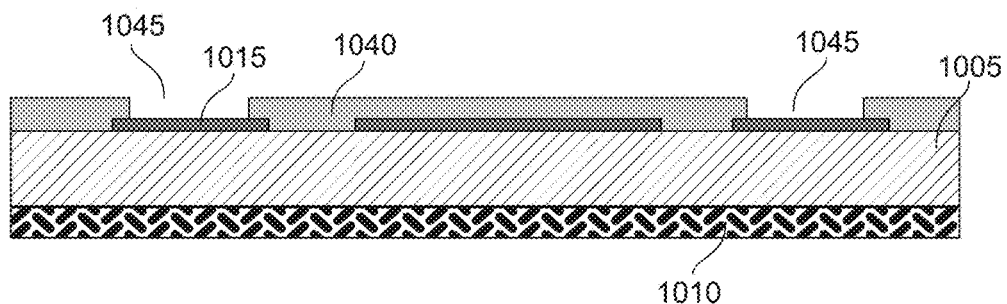

FIG. 10C shows a second polymer layer 1040 formed over the first polymer layer 1005 and the wiring layer 1015, and trenches 1045 formed within the second polymer layer 1040 to expose a at least a portion of a top surface of the wiring layer 1015. The second polymer layer 1040 may be comprised of a medical grade polymer material, for example, a soft polymer such as silicone or a polymer dispersion such as latex. In some embodiments, the second polymer layer 1040 may comprise silicone. In other embodiments, the second polymer layer 1040 may comprise latex, silicone, polytetrafluoroethylene (PTFE), perfluoroether (PFA), fluorinated ethylene propylene (FEP), polylactic acid (PLA), polyglycolic acid (PGA), polycaprolactone (PCL), polyether ether ketone (PEEK), and/or ethylene vinyl acetate (EVA).

The forming of the second polymer layer 1040 may include depositing and curing of a polymer material directly on the first polymer layer 1005 and the wiring layer 1015. For example, a solution comprised of polysiloxanes dissolved in a vaporizable organic solvent may be applied to the first polymer layer 1005 and the wiring layer 1015. The solution may then be heated at a temperature, preferably less than 250° C., to cure the polysiloxanes to form the desired silicone and vaporize the solvent. The second polymer layer 1040 may then be thinned to a desired thickness by planarization, grinding, wet etch, dry etch, oxidation followed by oxide etch, or any combination thereof. The second polymer layer 1040 may be plasma treated such that it forms a covalent bond to the first polymer layer 1005 to prevent separation of the materials and provide a moisture barrier. This process can be repeated to achieve a desired thickness for the second polymer layer 1040. In some embodiments, the second polymer layer 1040 may have a thickness from 2.0 μm to 40.0 μm. In some embodiments, the second polymer layer 1040 may have a thickness from 5.0 μm to 25.0 μm. In some embodiments, the second polymer layer 1040 may have a thickness from 10.0 μm to 20.0 μm.

In various embodiments, the trenches 1045 may be formed in the second polymer layer 1040 to expose at least a portion of a top surface of the wiring layer 1015. The trenches 1045 can be patterned using conventional lithographic, etching, and cleaning processes, to form the pattern of trenches 1045 shown in FIG. 10C, for example. For example, the trenches 1045 may be formed into the second polymer layer 1040 over the first portion of the wiring layer 1015 and the second portion of the wiring layer 1015 to expose at least a portion of a top surface of the wiring layer 1015. In some embodiments, a mask may be used to etch the trench patterns. Such a mask comprises a metal layer such as copper (Cu), gold (Au), silver (Ag), titanium (Ti), or platinum (Pt), or alloys thereof such as gold/chromium (Au/Cr) or Titanium/Platinum (Ti/Pt), and the second polymer layer 1040 may be etched using a plasma dry etch. Thereafter, the mask and substrate 1010 may be removed using processes that are well known in the art and thus, no further description is provided herein.

Figure 10D:
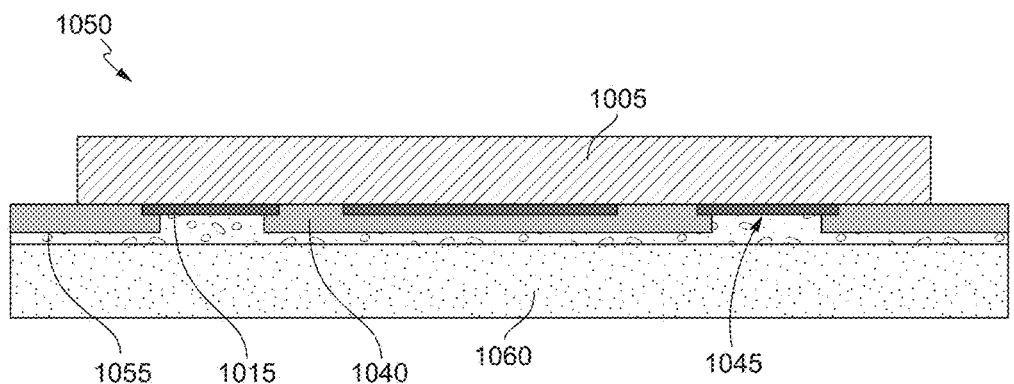

FIG. 10D shows an intermediate structure 1050 of the thin-film electrode assembly 1000 including the first polymer layer 1005, the wiring layer 1015, the second polymer layer 1040, and the trenches 1045 flipped upside down such that at least a top surface of the second polymer layer 1040 is temporarily bonded to an adhesive layer 1055 formed on a surface of a substrate 1060. The substrate 1060 may be comprised of but not limited to silicon, germanium, silicon germanium, silicon carbide, and those materials consisting essentially of one or more Group III-V compound semiconductors having a composition defined by the formula $Al_{X1}Ga_{X2}In_{X3}As_{Y1}P_{Y2}N_{Y3}Sb_{Y4}$, where X1, X2, X3, Y1, Y2, Y3, and Y4 represent relative proportions, each greater than or equal to zero and X1+X2+X3+Y1+Y2+Y3+Y4=1 (1 being the total relative mole quantity). Substrate 1060 may additionally or alternatively be comprised of Group II-VI compound semiconductors having a composition $Zn_{A1}Cd_{A2}Se_{B1}Te_{B2}$, where A1, A2, B1, and B2 are relative proportions each greater than or equal to zero and A1+A2+B1+B2=1 (1 being a total mole quantity). The processes to provide, obtain, or fabricate substrate 1060, as illustrated and described, are well known in the art and thus, no further description is provided herein.

The adhesive layer 1055 may be comprised of a thermoplastic temporary mounting adhesive, for example, a wash away adhesive such as Crystalbond™, Wafer-Mount™, or QuickStick™. In some embodiments, the forming of the intermediate structure 1050 flipped upside down on the adhesive layer 1055 and the substrate 1060 may include mixing a thermoplastic temporary mounting adhesive in a solution, depositing (e.g., spraying) the solution on a top surface of the substrate 1060, heating the solution to evaporate the solvents and form the adhesive layer 1055, pressing the upside down intermediate structure 1050 into the adhesive layer 1055 such that at least top surfaces of the second polymer layer 1040 is in directed contact with the adhesive layer 1055, and cooling at room temperature until the adhesive layer 1055 is completely dry and the intermediate structure 1050 is temporarily bonded to the substrate 1060. In alternative embodiments, the forming of the intermediate structure 1050 flipped upside down on the adhesive layer 1055 and the substrate 1060 may include heating a thermoplastic temporary mounting adhesive to a flow temperature, depositing (e.g., use of a mounting block) the adhesive on a top surface of the substrate 1060 to form the adhesive layer 1055, pressing the upside down intermediate structure 1050 into the adhesive layer 1055 such that at least a top surface of the second polymer layer 1040 is in directed contact with the adhesive layer 1055, and cooling at room temperature until the adhesive layer 1055 is completely dry and the intermediate structure 1050 is temporarily bonded to the substrate 1060.

Figure 10E:
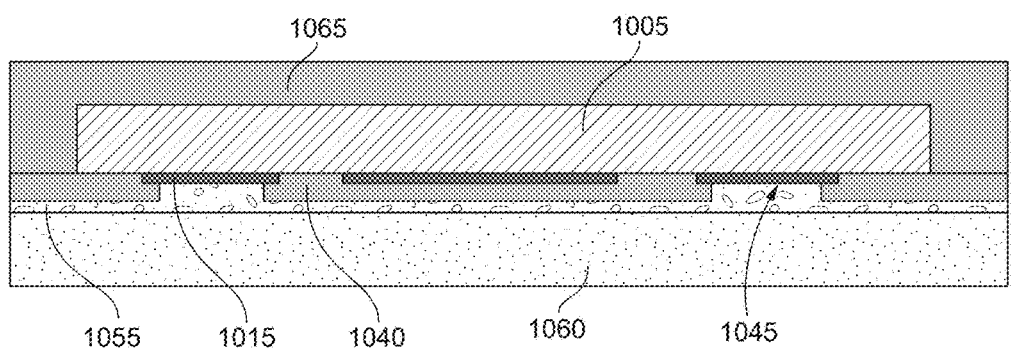

FIG. 10E shows a third polymer layer 1065 formed over the first polymer layer 1005 to the underlying adhesive layer 1055. The third polymer layer 1065 may be comprised of a medical grade polymer material, for example, a soft polymer such as silicone or a polymer dispersion such as latex. In some embodiments, the third polymer layer 1065 may comprise silicone. In other embodiments, the third polymer layer 1065 may comprise latex, silicone, polytetrafluoroethylene (PTFE), perfluoroether (PFA), fluorinated ethylene propylene (FEP), polylactic acid (PLA), polyglycolic acid (PGA), polycaprolactone (PCL), polyether ether ketone (PEEK), and/or ethylene vinyl acetate (EVA).

The forming of the third polymer layer 1065 may include depositing and curing of a polymer material directly on a bottom surface of the first polymer layer 1005 and the underlying adhesive layer 1055. For example, a solution comprised of polysiloxanes dissolved in a vaporizable organic solvent may be applied to a bottom surface of the first polymer layer 1005 and the underlying adhesive layer 1055. The solution may then be heated at a temperature, preferably less than 250° C., to cure the polysiloxanes to form the desired silicone and vaporize the solvent. A surface of the third polymer layer 1065 may be coplanar with a top surface of the first polymer layer 1005. The third polymer layer 1065 may then be thinned to a desired thickness by planarization, grinding, wet etch, dry etch, oxidation followed by oxide etch, or any combination thereof. This process can be repeated to achieve a desired thickness for the third polymer layer 1065. The third polymer layer 1065 may be plasma treated such that it forms a covalent bond to the first polymer layer 1005 to prevent separation of the materials and provide a moisture barrier. In some embodiments, the third polymer layer 1065 may have a thickness from 100.0 μm to 500.0 μm. In some embodiments, the third polymer layer 1065 may have a thickness from 200.0 μm to 400.0 μm. In some embodiments, the third polymer layer 1065 may have a thickness from 250.0 μm to 350.0 μm.

Figure 10F:
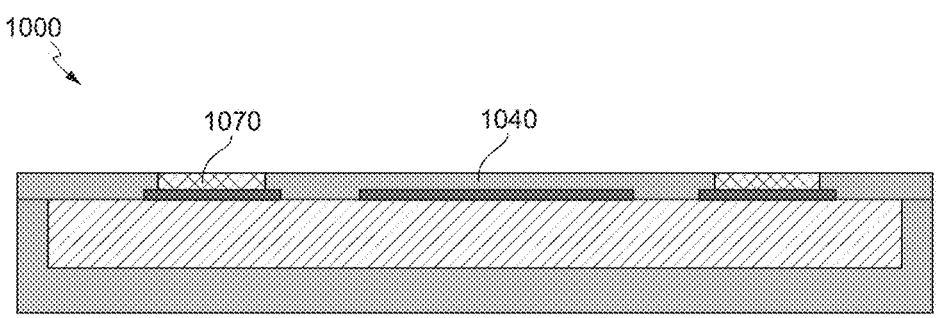

FIG. 10F shows the thin-film electrode assembly 1000 including the first polymer layer 1005, the wiring layer 1015, the second polymer layer 1040, and the third polymer layer 1065 detached from the adhesive layer 1055 and the substrate 1060, and flipped topside up. In some embodiments, detaching the thin-film electrode assembly 100 from the adhesive layer 1055 and the substrate 1060 may include removal of the adhesive (e.g., applying a stripper solution to dissolve the adhesive), and cleaning (e.g., a step-wise rinsing process) at least top surfaces of the wiring layer 1015, the second polymer layer 1040, and the third polymer layer 1065 with acetone, isopropyl alcohol, non-ionic surfactant, a liquid detergent system, and/or deionized water to remove residual material such as remaining adhesive material.

FIG. 10F also shows one or more electrodes 1070 formed in a pattern within the trenches 1045 of the second polymer layer 1040. In some embodiments, forming the electrodes 1070 may include depositing a seed layer (e.g., a copper (Cu) seed layer, a gold (Au) seed layer, a silver (Ag) seed layer, a gold/chromium (Au/Cr) seed layer, etc.) within the trenches 1045 of the second polymer layer 1040. The seed layer may be configured to enable forming of a wire on the second polymer layer 1040 (e.g., through Cu electroplating, Au electroplating, Sn electroplating, Ag electroplating, Au/Cr electroplating, etc.). Optionally, and prior to forming of the seed layer, an adhesion layer may be deposited over the second polymer layer 1040 to enable adequate application of the seed layer. Deposition of either or both of the adhesion layer and seed layer may include sputter deposition without or without lithographic process, e.g., application of a resist mask.

Following deposition of the seed layer, a resist pattern may be formed above the second polymer layer 1040. The resist pattern may include openings that align over at least a trench 1045 of the second polymer layer 1040 for forming of an electrode 1070. For example, the resist may be patterned with openings to form: (i) a first electrode 1070 within a first trench 1045 of the second polymer layer 1040, and (ii) a second electrode 1070 within a second trench 1045 of the second polymer layer 1040. It should be understood by those of skill in the art that different patterns are also contemplated by the present invention.

In various embodiments, electrode 1070 may be deposited through electroplating (e.g., through Cu electroplating, Au electroplating, Sn electroplating, Ag electroplating, Au/Cr electroplating, etc.) and may be positioned over at least a portion of the second polymer layer 1040. The electroplating may be performed at a current density of about 4.0 mA/cm2 to about 4.5 mA/cm2. In some embodiments, the exposed area or portion of the substrate may encompass about 8 cm2 to about 10 cm2. The current may be about 14 mA to about 18 mA and the duration may be from about 110 minutes to about 135 minutes to form the electrode 1070 having a thickness of about 5 µm to about 25 µm. In other embodiments, the exposed area or portion of the substrate may encompass about 10 cm2 to about 18 cm2. The current may be about 18 mA to about 28 mA and the duration may be from about 35 minutes to about 50 minutes to form the electrode having a thickness of about 1 µm to about 5 µm.

Following the deposition of the electrode 1070, the intermediate structure may be subjected to a strip resist to remove the resist pattern and expose portions of the seed layer (portions without wire formation), and optionally the adhesion layer. The exposed portions of the seed layer, and optionally the adhesion layer, may then be subjected to an etch (e.g., wet etch, dry etch, etc.) to remove those portions, thereby isolating the electrode 1070 within the trench 1045.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A thin-film electrode assembly comprising:
   an overmold comprising a first polymer;
   a supporting structure formed within a portion of the overmold, wherein the supporting structure comprises a second polymer, different from the first polymer;
   a wire formed within a portion of the supporting structure;
   an electrode formed on a top surface of the supporting structure and in electrical contact with the wire,
   wherein the electrode comprises a top surface that is raised above a top surface of the overmold by a predetermined distance;
   another supporting structure formed within another portion of the overmold;
   another wire formed within a portion of the another supporting structure; and
   another electrode formed on a top surface of the another supporting structure and in electrical contact with the another wire,
   wherein the another electrode comprises a top surface that is raised above the top surface of the overmold by the predetermined distance, and
   wherein the supporting structure and the electrode are isolated from the another supporting structure and the another electrode by a region of the overmold.

2. The thin-film electrode assembly of claim 1, wherein the first polymer layer comprises polyimide or liquid crystal polymer (LCP), and the second polymer layer comprises silicone.

3. The thin-film electrode assembly of claim 1, further comprising a contact formed within the portion of the supporting structure that provides the electrical contact between the electrode and the wire.

4. The thin-film electrode assembly of claim 1, wherein the top surface of the supporting structure is coplanar with the top surface of the overmold.

5. The thin-film electrode assembly of claim 1, wherein the wire is embedded within the portion of the supporting structure.

6. The thin-film electrode assembly of claim 1, wherein the supporting structure is embedded within the overmold.

7. The thin-film electrode assembly of claim 1, further comprising an additional supporting structure formed within the region of the overmold, and an additional wire formed within a portion of the additional supporting structure,
   wherein the supporting structure and the electrode are isolated from the additional supporting structure by a first portion of the region of the overmold and the another supporting structure and the another electrode are isolated from the additional supporting structure by a second portion of the region of the overmold; and
   wherein the supporting structure and the another supporting structure have a first shape that are non-expandable, and the additional supporting structure has a second shape that is expandable.

8. The thin-film electrode assembly of claim 1, further comprising an additional supporting structure formed within the region of the overmold, wherein the supporting structure and the electrode are isolated from the additional supporting structure by a first portion of the region of the overmold and the another supporting structure and the another electrode are isolated from the additional supporting structure by a second portion of the region of the overmold.

9. The thin-film electrode assembly of claim 8, further comprising an additional wire formed within a portion of the additional supporting structure, wherein a top surface of the additional supporting structure is coplanar with the top surface of the overmold, the supporting structure, and the another supporting structure.

10. The thin-film electrode assembly of claim 9, wherein the wire is embedded within the portion of the supporting structure, the another wire is embedded within the portion of the another supporting structure, and the additional wire is embedded within the portion of the additional supporting structure.

11. The thin-film electrode assembly of claim 1, wherein the predetermined distance is greater than 0.5 µm.

12. A thin-film electrode assembly comprising:
    an overmold comprising silicone;
    a first support structure within a first portion of the overmold, wherein the first support structure includes polyimide or liquid crystal polymer (LCP) and a wire, and the first support structure has a first shape that is non-expandable;
    a second support structure within a second portion of the overmold, wherein the second support structure includes the polyimide or LCP and the wire, and the second support structure has a second shape that is different from the first shape that is expandable; and
    an electrode formed on a top surface of the first supporting structure and in electrical contact with the wire, wherein the electrode comprises a top surface that is raised above a top surface of the overmold by a predetermined distance.

13. The thin-film electrode assembly of claim 12, further comprising one or more contact pads in electrical contact with the wire.

14. The thin-film electrode assembly of claim 12, further comprising a contact formed within first support structure that provides electrical contact between the electrode and the wire.

15. The thin-film electrode assembly claim 12, further comprising:
    a third support structure within a third portion of the overmold, wherein the third support structure includes the polyimide or LCP and the wire, and the third support structure has the first shape;

another electrode formed on a top surface of the third supporting structure and in electrical contact with the wire; and a fourth support structure within a fourth portion of the overmold, wherein the fourth support structure includes the polyimide or LCP and the wire, and the fourth support structure has the second shape.

16. The thin-film electrode assembly of claim 15, wherein the first support structure is in physical contact with the second support structure, the third support structure is in physical contact with the second support structure and the fourth support structure, and the third support structure is isolated from the first support structure by the second support structure and the overmold.

17. The thin-film electrode assembly of claim 12, wherein the predetermined distance is greater than 0.5 μm.

* * * * *